(12) United States Patent
Grego et al.

(10) Patent No.: US 12,339,200 B2
(45) Date of Patent: Jun. 24, 2025

(54) EXCRETA SAMPLING TOILET AND INLINE SPECIMEN ANALYSIS SYSTEM AND METHOD

(71) Applicant: DUKE UNIVERSITY, Durham, NC (US)

(72) Inventors: Sonia Grego, Durham, NC (US); Brian T. Hawkins, Durham, NC (US); Katelyn L Sellgren, Durham, NC (US); Brian R. Stoner, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 378 days.

(21) Appl. No.: 17/800,744

(22) PCT Filed: Feb. 19, 2021

(86) PCT No.: PCT/US2021/018765
§ 371 (c)(1),
(2) Date: Aug. 18, 2022

(87) PCT Pub. No.: WO2021/168237
PCT Pub. Date: Aug. 26, 2021

(65) Prior Publication Data
US 2023/0102589 A1    Mar. 30, 2023

Related U.S. Application Data

(60) Provisional application No. 62/978,414, filed on Feb. 19, 2020.

(51) Int. Cl.
*G01N 1/20* (2006.01)
*E03C 1/26* (2006.01)
(Continued)

(52) U.S. Cl.
CPC .............. *G01N 1/2035* (2013.01); *E03C 1/26* (2013.01); *G01N 1/38* (2013.01); *G06T 7/0012* (2013.01);
(Continued)

(58) Field of Classification Search
CPC ........... G01N 1/2035; G01N 2001/205; G01N 2001/2057; G01N 2001/383; E03C 1/26; E03C 1/262; G06T 7/0012; A61B 10/0038
See application file for complete search history.

(56) References Cited

U.S. PATENT DOCUMENTS 4,860,767 A    8/1989    Maekawa
4,961,431 A    10/1990   Ikenaga et al.
(Continued)

FOREIGN PATENT DOCUMENTS

CN    107034968 A    8/2017
WO    2018237265 A1  12/2018

OTHER PUBLICATIONS

Exact Sciences Corporation, "Total 2018 Revenue Increased 71 Percent to $454 Million, and 934,000 People Were Screened With Cologuard," Cision PR Newswire, Feb. 21, 2019, 7 pages.
(Continued)

*Primary Examiner* — Reinaldo Sanchez-Medina
(74) *Attorney, Agent, or Firm* — Talem IP Law, LLP

(57) ABSTRACT

An excreta sample capture device includes a primary influent pipe that receives influent from a toilet(s) and includes an upstream end and a downstream end. The excreta sample capture device also includes a first valve positioned at the downstream end of the primary influent pipe, and a second valve positioned between the upstream end and the downstream end of the primary influent pipe. In some cases, an excreta sample capture device further includes spray jet
(Continued)

positioned above the second valve and a sample extraction vessel located downstream from the second valve. A method of using an excreta sample capture device includes receiving influent in the primary influent pipe, initiating a closing of the first valve, opening the second valve, and capturing a sample of the excreta.

13 Claims, 11 Drawing Sheets

(51) Int. Cl.
    *G01N 1/38*     (2006.01)
    *G06T 7/00*     (2017.01)

(52) U.S. Cl.
    CPC ............ *G01N 2001/205* (2013.01); *G06T 2207/30004* (2013.01)

(56) References Cited

U.S. PATENT DOCUMENTS

| | | | |
|---|---|---|---|
| 5,073,500 | A | 12/1991 | Saito et al. |
| 5,772,606 | A * | 6/1998 | Ashibe ............... G01N 21/359 |
| | | | 600/584 |
| 9,810,686 | B1 | 11/2017 | Hall et al. |
| 10,258,261 | B2 | 4/2019 | Hall et al. |
| 11,604,177 | B1 * | 3/2023 | Park ..................... G01N 31/22 |
| 2014/0075886 | A1 | 3/2014 | Bell |
| 2015/0359522 | A1 | 12/2015 | Recht et al. |
| 2017/0067806 | A1 * | 3/2017 | Dewar ..................... G01N 1/38 |
| 2017/0322197 | A1 | 11/2017 | Hall et al. |
| 2018/0055491 | A1 | 3/2018 | Hall et al. |
| 2018/0168556 | A1 | 6/2018 | Hall et al. |
| 2018/0321218 | A1 | 11/2018 | Hall et al. |
| 2019/0062813 | A1 | 2/2019 | Amin |

OTHER PUBLICATIONS

Ranjitkar, Pratistha, "Toilet Lab: Diagnostic Tests on Smart Toilets" Clinical Chemistry, Jul. 1, 2018, pp. 1128-1129, vol. 64, issue 7.
Axup, Jun, "Clinicai: Detecting Colorectal Cancer in Your Toilet," Medium, Nov. 1, 2018, 4 pages.
Lessa, Fernanda C. et al., "Burden of Clostridium difficile Infection in the United States," New England Journal of Medicine, Jun. 11, 2015 (Accessible: Feb. 26, 2015), pp. 2368-2370, vol. 372, issue 9.
Qiagen, "User-Developed Protocol: Isolation of viral RNA from stool using the QIAamp® Viral RNA Mini Kit", Jun. 10, 2021, 2 pages.
Mettler Toledo, "InPro 8050 Turbidity Probe", 2022, Mettler Toledo Group—Process Analytics, 2 pages.
Dorman, William , "Specimen Collection and Submission Manual," Jun. 1, 2016, USAMRIID—Special Pathogens Laboratory, Fort Belvoir, VA, 25 pages.
Wald, Chelsea, "Diagnostics: A flow of information," Nature, Nov. 9, 2017, pp. S48-50, vol. 551, issue 7679.
Said, Maria A. et al., "Healthcare Epidemiology: Gastrointestinal Flu: Norovirus in Health Care and Long-Term Care Facilities," Clinical Infectious Diseases, Nov. 1, 2008, pp. 1202-1208, vol. 47, issue 9.
James Thorne, "Naveen Jain's wellness startup Viome to acquire Habit nutrition service from Campbell Soup Co.," GeekWire, Feb. 6, 2019, 2 pages.
International Search Report and Written Opinion issued in International Application No. PCT/US2021/018765, mailed Jun. 15, 2021, 12 pages.
ReportLinker, "Microbiome Therapeutics and Diagnostics Market (2nd Edition), 2017-2030," Cision PR Newswire, Aug. 28, 2017, 10 pages.
Weintrob, Amy C. et al., "Active surveillance for asymptomatic colonization with multidrug-resistant gram negative bacilli among injured service members—a three year evaluation," MSMR, Aug. 2013, pp. 17-22, vol. 20, issue 8.
Young, Graeme P. et al., "Advances in Fecal Occult Blood Tests: The FIT Revolution," Digestive Diseases and Sciences, Mar. 2015 (Accessible Dec. 10, 2014), pp. 609-622, vol. 60, issue 3.
Bijos, Artur et al., "The usefulness of ultrasound examination of the bowel as a method of assessment of functional chronic constipation in children," Pediatric Radiology, Nov. 14, 2007 (Accessible: Oct. 19, 2007), pp. 1247-1252, vol. 37, issue 12.
Cheng, Vincent C. C. et al., "Control of Carbapenemase-producing Enterobacteriaceae: Beyond the Hospital," EClinicalMedicine, Dec. 2018, pp. 3-4, vol. 6.
Cho, Ilseung et al., "The human microbiome: at the interface of health and disease," Nature Reviews Genetics, Apr. 2012 (Accessible: Mar. 13, 2012), pp. 260-270, vol. 13, issue 4.
Ginsburg, Geoffrey S et al., "Precision Medicine: From Science to Value," Health Affairs, May 2018, pp. 694-701, vol. 37, issue 5.
Gu, Yan-Hong et al., "Stool Color Card Screening for Early Detection of Biliary Atresia and Long-Term Native Liver Survival: A 19-Year Cohort Study in Japan," The Journal of Pediatrics, Apr. 2015 (Accessible: Feb. 10, 2015), pp. 897-902.e1, vol. 166, issue 4.
Hanai, Akiko et al., "Effects of a self-management program on antiemetic-induced constipation during chemotherapy among breast cancer patients: a randomized controlled clinical trial," Breast Cancer Research and Treatment, Jan. 2016 (Accessible: Dec. 9, 2015), pp. 99-107, vol. 155, issue 1.
Hawkins, Brian T. et al., "Electrochemical disinfection of repeatedly recycled blackwater in a free-standing, additive-free toilet," Water and Environment Journal, Nov. 2017, pp. 545-551, vol. 31, issue 4.
Ibrahim, Mohamed et al., "Cyberphysical Digital-Microfluidic Biochips: Bridging the Gap Between Microfluidics and Microbiology," Proceedings of the IEEE, Sep. 2018 (Accessible: Oct. 30, 2017), 6 pages, vol. 106, issue 9.
Ibrahim, Mohamed et al., "Synthesis of a Cyberphysical Hybrid Microfluidic Platform for Single-Cell Analysis," IEEE Transactions on Computer-Aided Design of Integrated Circuits and Systems, Jul. 2019 (Accessible: Jun. 12, 2018), 15 pages, vol. 38, issue 7.
Johnson, Colin D. et al., "Qualitative Assessment of the Symptoms and Impact of Pancreatic Exocrine Insufficiency (PEI) to Inform the Development of a Patient-Reported Outcome (PRO) Instrument," The Patient—Patient-Centered Outcomes Research, Oct. 2017 (Accessible: Mar. 22, 2017), pp. 615-628, vol. 10, issue 5.
Liang, Tung-Che et al., "Multitarget Sample Preparation Using MEDA Biochips," IEEE Transactions on Computer-Aided Design of Integrated Circuits and Systems, Oct. 2020 (Accessible: Sep. 17, 2019), pp. 2682-2695, vol. 39, issue 10.
Majid, Hazreen A. et al., "Definitions, Attitudes, and Management Practices in Relation to Diarrhea During Enteral Nutrition: A Survey of Patients, Nurses, and Dietitians," Nutrition in Clinical Practice, Apr. 2012, pp. 252-260, vol. 27, issue 2.
Markland, Alayne D. et al., "Association of Low Dietary Intake of Fiber and Liquids With Constipation: Evidence From the National Health and Nutrition Examination Survey," American Journal of Gastroenterology, May 2013 (Accessible: Apr. 9, 2013), 18 pages, vol. 108, issue 5.
Ohno, Harumi et al., "Validity of an observational assessment tool for multifaceted evaluation of faecal condition," Scientific Reports, Mar. 6, 2019, (Accessible: Mar. 6, 2019), p. 3760, vol. 9, issue 1.
Palsson, Olafur S. et al., "IBS Patients Show Frequent Fluctuations Between Loose/Watery and Hard/Lumpy Stools: Implications for Treatment," American Journal of Gastroenterology, Feb. 2012 (Accessible: Nov. 8, 2011), 21 pages, vol. 107, issue 2.
Peery, Anne F. et al., "Burden and Cost of Gastrointestinal, Liver, and Pancreatic Diseases in the United States: Update 2018," Gastroenterology, Jan. 2019 (Accessible: Oct. 10, 2018), 39 pages, vol. 156, issue 1.
Rogers, Tate W. et al., "A granular activated carbon/electrochemical hybrid system for onsite treatment and reuse of blackwater," Water Research, Nov. 2018 (Accessible: Jul. 30, 2018), pp. 553-560, vol. 144.
Tanaka, Shiho et al., "Fecal Distribution Changes Using Colorectal Ultrasonography in Older People with Physical and Cognitive Impairment Living in Long-Term Care Facilities: A Longitudinal

(56) References Cited

OTHER PUBLICATIONS

Observational Study," Healthcare, May 25, 2018 (Accessible: May 25, 2018), 15 pages, vol. 6, issue 2, article 55.
Vandeputte, Doris et al., "Water activity does not shape the microbiota in the human colon," Gut, Oct. 2017 (Accessible: Jan. 6, 2017), pp. 1865-1866, vol. 66, issue 10.
Vandeputte, Doris et al., "Stool consistency is strongly associated with gut microbiota richness and composition, enterotypes and bacterial growth rates," Gut, Jan. 2016 (Accessible: Jun. 11, 2015), pp. 57-62, vol. 65, issue 1.
Welling, Claire M. et al., "Field testing of a household-scale onsite blackwater treatment system in Coimbatore, India," Science of The Total Environment, Apr. 2020 (Accessible: Jan. 15, 2020), 9 pages, vol. 713, article 136706.
Yabunaka, Koichi et al., "Sonographic Visualization of Fecal Loading in Adults: Comparison With Computed Tomography," Journal of Diagnostic Medical Sonography, Mar. 2015 (Accessible: Jan. 13, 2015), pp. 86-92, vol. 31, issue 2.
Yang, Patricia J. et al., "Hydrodynamics of defecation," Soft Matter, Aug. 2017 (Accessible: Apr. 25, 2017), pp. 4960-4970, vol. 13, issue 29.
Zuckerman, Gary R. et al., "An objective measure of stool color for differentiating upper from lower gastrointestinal bleeding," Digestive Diseases and Sciences, Aug. 1995, pp. 1614-1621, vol. 40, issue 8.
Buss, Sarah N. et al., "Multicenter Evaluation of the BioFire FilmArray Gastrointestinal Panel for Etiologic Diagnosis of Infectious Gastroenteritis," Journal of Clinical Microbiology, Mar. 2015 (Accessible Jan. 14, 2015), pp. 915-925, vol. 53, issue 3.
Byrne, Barry et al., "Antibody-Based Sensors: Principles, Problems and Potential for Detection of Pathogens and Associated Toxins," Sensors, Jun. 5, 2009, pp. 4407-4445, vol. 9, issue 6.
De Paz, Hector David et al., "Molecular isothermal techniques for combating infectious diseases: towards low-cost point-of-care diagnostics," Expert Review of Molecular Diagnostics, Sep. 2014, pp. 827-843, vol. 14, issue 7.
Drancourt, Michel et al., "The Point-of-Care Laboratory in Clinical Microbiology," Clinical Microbiology Reviews, Jul. 2016 (accessible Mar. 30, 2016), pp. 429-447, vol. 29, issue 3.
Fan, Fenxia et al., "The Development and Evaluation of a Loop-Mediated Isothermal Amplification Method for the Rapid Detection of Salmonella enterica serovar Typhi," PLOS ONE, Apr. 24, 2015, pp. 1-13, vol. 10, issue 4.
Figueroa, Carmen et al., "Reliability of HIV rapid diagnostic tests for self-testing compared with testing by health-care workers: a systematic review and meta-analysis," The Lancet HIV, Jun. 2018 (Accessible Apr. 24, 2018), pp. e277-90, vol. 5, issue 6.
Lee, Marilyn B. et al., "A Review of Gastrointestinal Outbreaks in Schools: Effective Infection Control Interventions," Journal of School Health, Dec. 2010, pp. 588-598, vol. 80, issue 12.
Ma, Duo et al., "Low-cost detection of norovirus using paper-based cell-free systems and synbody-based viral enrichment," Synthetic Biology, Jan. 1, 2018 (Accessible Sep. 19, 2018), pp. 1-11, vol. 3, issue 1.
Matias, Wilfredo R. et al., "Laboratory evaluation of immunochromatographic rapid diagnostic tests for cholera in Haiti," PLOS ONE, Nov. 1, 2017, pp. 1-12, vol. 12, issue 11.
Peng, Zhong et al., "Advances in the diagnosis and treatment of Clostridium difficile infections," Emerging Microbes & Infections, Dec. 1, 2018, pp. 1-13, vol. 7, issue 1.
Aylin Sertkaya et al., "Economic Incentives for the Development of Rapid Point-of-Care (POC) Diagnostic Devices for C. Difficile, Carbapenem-Resistant Enterobacteriaceae (CRE), and Neisseria Gonorrhoeae", Report prepared for U.S. Department of Health and Human Services, Oct. 12, 2018, 77 pages, Eastern Research Group, Inc., Lexington, MA.
Verosloff, M. et al., "PLANT-Dx: A Molecular Diagnostic for Point-of-Use Detection of Plant Pathogens," ACS Synthetic Biology, Apr. 19, 2019 (Accessible Feb. 21, 2019), pp. 902-905, vol. 8, issue 4.

Lewis, S. J. et al., "Stool Form Scale as a Useful Guide to Intestinal Transit Time," Scandinavian Journal of Gastroenterology, Jan. 1997, pp. 920-924, vol. 32, issue 9.
Woolley, S. M. et al., "Rheological modelling of fresh human faeces," Journal of Water, Sanitation and Hygiene for Development, Sep. 1, 2014, pp. 484-489, vol. 4, issue 3.
Septimus, Edward et al., "Approaches for Preventing Healthcare-Associated Infections: Go Long or Go Wide" Infection Control and Hospital Epidemiology, Jul. 2014, pp. 797-801, vol. 35, issue 7.
Broadhurst, M. Jana et al., "Diagnosis of Ebola Virus Disease: Past, Present, and Future," Clinical Microbiology Reviews, Oct. 2016 (accessible Jul. 13, 2016), pp. 773-793, vol. 29, issue 4.
Sahondo, Tapuwa et al., "Field testing of a household-scale onsite blackwater treatment system in South Africa," Science of The Total Environment, Feb. 2020 (Accessible Nov. 11, 2019), pp. 1-9, vol. 703.
Asghar, Humayun et al., "Environmental Surveillance for Polioviruses in the Global Polio Eradication Initiative," Journal of Infectious Diseases, Nov. 1, 2014, pp. S294-303, vol. 210, issue suppl 1.
Daughton, Christian G., "Monitoring wastewater for assessing community health: Sewage Chemical-Information Mining (SCIM)," Science of The Total Environment, Apr. 2018 (Accessible Nov. 29, 2017), pp. 748-764, vol. 619-620.
Lerner, A. et al., "Rectal Swabs Are Suitable for Quantifying the Carriage Load of KPC-Producing Carbapenem-Resistant Enterobacteriaceae," Antimicrobial Agents and Chemotherapy, Mar. 2013 (Accessible Jan. 7, 2013), pp. 1474-1479, vol. 57, issue 3.
Ra, Moonsoo et al., "Smartphone-Based Point-of-Care Urinalysis Under Variable Illumination," IEEE Journal of Translational Engineering in Health and Medicine, Jan. 9, 2018 (Accessible Dec. 16, 2017), 11 pages, vol. 6.
Kim, Huijae et al., "Using Digital Filters to Obtain Accurate Trended Urine Glucose Levels from Toilet-Deployable Near-Infrared Spectrometers," Journal of Analytical & Bioanalytical Techniques, 2016, pp. 1-4, vol. 7, issue 5.
Gambhir, Sanjiv Sam et al., "Toward achieving precision health," Science Translational Medicine, Feb. 28, 2018 (Accessible Jun. 4, 2018), pp. 1-12, vol. 10, issue 430.
Tsang, W. C. et al., "Validation of the TOTO Flowsky® uroflowmetry device," European Urology Supplements, Mar. 2017, pp. e1959-60, vol. 16, issue 3.
Hachuel, David et al., "Augmenting gastrointestinal health: a deep learning approach to human stool recognition and characterization in macroscopic images," ArXiv Preprint ArXiv: 1903. 10578, Mar. 25, 2019 (Accessible Dec. 4, 2018), 8 pages.
Conn, Nicholas J. et al., "In-Home Cardiovascular Monitoring System for Heart Failure: Comparative Study," JMIR MHealth and UHealth, Jan. 18, 2019 (Accessible Oct. 4, 2018), page e12419 (1-12), vol. 7, issue 1.
Zhou, Jin et al., "Sensor-Array Optimization Based on Time-Series Data Analytics for Sanitation-Related Malodor Detection," IEEE Transactions on Biomedical Circuits and Systems, Aug. 17, 2020 (Accessible: Jun. 12, 2020), pp. 705-714, vol. 14, issue 4.
Allison, James E. et al., "Population Screening for Colorectal Cancer Means Getting FIT: The Past, Present, and Future of Colorectal Cancer Screening Using the Fecal Immunochemical Test for Hemoglobin (FIT)," Gut and Liver, Mar. 2, 2014, pp. 117-130, vol. 8, issue 2.
Barrett, Timothy J. et al., "Use of Moore swabs for isolating Vibrio cholerae from sewage," Journal of Clinical Microbiology, Apr. 1980, pp. 385-388, vol. 11, issue 4.
US Preventive Services Task Force et al., "Screening for Colorectal Cancer: US Preventive Services Task Force Recommendation Statement," JAMA, Jun. 21, 2016, pp. 2564-2575, vol. 315, issue 23.
Brown, Joe et al., "Stool-Based Pathogen Detection Offers Advantages as an Outcome Measure for Water, Sanitation, and Hygiene Trials," The American Journal of Tropical Medicine and Hygiene, Feb. 5, 2020 (Accessible Nov. 4, 2019), pp. 260-261, vol. 102, issue 2.
Chiang, Cheng-Ta, Onyema Greg et al., "Development of a Calibrated Transducer CMOS Circuit for Water Turbidity Monitoring," IEEE Sensors Journal, Jun. 1, 2016, pp. 4478-4483, vol. 16, issue 11.

(56) References Cited

OTHER PUBLICATIONS

Chido-Amajuoyi et al., "Physician-office vs home uptake of colorectal cancer screening using FOBT/FIT among screening-eligible US adults," Cancer Medicine, Dec. 2019 (Accessible Oct. 21, 2019), pp. 7408-7418, vol. 8, issue 17.
Daly, Jeanette M. et al., "Which Fecal Immunochemical Test Should I Choose," Journal of Primary Care & Community Health, Oct. 2017 (Accessible Apr. 27, 2017), pp. 264-277, vol. 8, issue 4.
Elias, Sjoerd G. et al., "Is there an added value of faecal calprotectin and haemoglobin in the diagnostic work-up for primary care patients suspected of significant colorectal disease? A cross-sectional diagnostic study," BMC Medicine, Dec. 2016 (Accessible Sep. 26, 2016), 11 pages, vol. 14, issue 1.
Wang, Youchao et al., "Low-Cost Turbidity Sensor for Low-Power Wireless Monitoring of Fresh-Water Courses," IEEE Sensors Journal, Jun. 1, 2018 (Accessible Apr. 13, 2018), pp. 4689-4696, vol. 18, issue 11.
Lambrou, Theofanis p et al., "A Low-Cost Sensor Network for Real-Time Monitoring and Contamination Detection in Drinking Water Distribution Systems," IEEE Sensors Journal, Aug. 2014 (Accessible Apr. 10, 2014), pp. 2765-2772, vol. 14, issue 8, IEEE.
Park, Seung-Min et al., "A mountable toilet system for personalized health monitoring via the analysis of excreta," Nature Biomedical Engineering, Apr. 6, 2020 (Accessible Jul. 23, 2020), pp. 624-635, vol. 4, issue 6.
Penn, Roni et al., "Review of synthetic human faeces and faecal sludge for sanitation and wastewater research," Water Research, Apr. 2018 (Accessible Dec. 30, 2017), pp. 222-240, vol. 132.
Pham, Robyn et al., ""Finding the Right FIT": Rural Patient Preferences for Fecal Immunochemical Test (FIT) Characteristics," The Journal of the American Board of Family Medicine, Sep. 18, 2017, pp. 632-644, vol. 30, issue 5.
Rose, C. et al., "The Characterization of Feces and Urine: A Review of the Literature to Inform Advanced Treatment Technology," Critical Reviews in Environmental Science and Technology, Sep. 2, 2015 (Accessible May 29, 2015), pp. 1827-1879, vol. 45, issue 17.
Shulman, Lester M. et al., "Evaluation of Four Different Systems for Extraction of RNA from Stool Suspensions Using MS-2 Coliphage as an Exogenous Control for RT-PCR Inhibition," PLoS ONE, Jul. 16, 2012, p. e39455 (1-8), vol. 7, issue 7.
Van Roon, Aafke H. C. et al., "Random comparison of repeated faecal immunochemical testing at different intervals for population-based colorectal cancer screening," Gut, Mar. 2013 (Accessible 2012), 16 pages, vol. 62, issue 3.
Vandenberg, Nicholas et al., "Extraction of human nuclear DNA from feces samples using the QIAamp DNA Stool Mini Kit.," Journal of Forensic Sciences, Sep. 1, 2002 (Accessible Jul. 17, 2002), pp. 993-995, vol. 47, issue 5.
Vineetha, K. V. et al., "Performance analysis of MEMS sensor for the detection of cholera and diarrhea," Microsystem Technologies, Sep. 2018 (Accessible Mar. 5, 2018), pp. 3705-3712, vol. 24, issue 9.

\* cited by examiner

EXCRETA SAMPLING TOILET AND INLINE SPECIMEN ANALYSIS SYSTEM AND METHOD

CROSS-REFERENCE TO RELATED APPLICATIONS

This application is the U.S. National Stage Application of International Application No. PCT/US21/18765, filed Feb. 19, 2021, which claims the benefit of U.S. Provisional Patent Application Ser. No. 62/978,414, filed Feb. 19, 2020, which are hereby incorporated by reference in their entirety.

BACKGROUND

Human excreta (e.g., urine and/or feces) can be analyzed for multitudes of valuable health and wellness data for individuals and populations of people. For example, visual, chemical, immunological, and/or molecular analysis can be performed on excreta to help diagnose and treat acute/chronic gastrointestinal conditions, such as Irritable Bowel Syndrome, cancer, and Crohn's Disease, as well as individual information for gut microbiota. Furthermore, other valuable information can be gleaned from excreta, including community level data on alcohol consumption, pharmaceuticals, illicit drug use, and pollutants exposure. Excreta can also be used to detect outbreaks of infectious diseases, including SARS-CoV-2, norovirus and antibiotic-resistant bacteria.

However, excreta collection for analysis is typically underutilized because it requires invasive capture/collection methods. Indeed, the common dislike of handling excreta (e.g., the "ick factor"), patient reluctance to report on bowel movements, and burden of constant tracking of bowel movements have prevented the widespread use of excreta samples for health and wellness analysis.

BRIEF SUMMARY

Excreta sampling toilet and inline specimen analysis systems and methods are provided. An excreta sample capture device as described herein provides a way to get the valuable health and wellness information for individuals and populations of people without requiring any handling of the excreta by the user. Advantageously, users may simply flush the toilet (as they normally would when using the restroom) and their excreta is automatically captured and available for analysis. The resulting analysis can provide individualized and/or community data on users' health and well-being. Indeed, the automated capture of excreta samples can provide individuals and the public with all of the benefits of using excreta samples for diagnosis and evaluation of treatment regimens, as well as the benefit of information that is not normally obtained from excreta samples such as information gleaned from uniform optical imaging and/or gas detection.

An excreta sample capture device includes a primary influent pipe that receives influent from one or more toilets; a first valve positioned at a downstream end of the primary influent pipe; and a second valve positioned underneath and between an upstream end of the primary influent pipe and the downstream end of the primary influent pipe. In some cases, the excreta sample capture device further includes a spray jet positioned above the second valve. In some cases, the excreta sample capture device further includes a sample extraction vessel located downstream from the second valve. In some cases, the spray jet is configured to provide a jet of liquid to the second valve. In some cases, the excreta sample capture device further includes a second spray jet configured to provide a jet of cleaning fluid to the primary influent pipe.

In some cases, the excreta sample capture device further includes a third valve positioned upstream of the first valve; and a secondary influent pipe positioned underneath the third valve that reconnects to piping downstream of the primary influent pipe. In some cases, the third valve is radially adjacent to the second valve and the secondary influent pipe is sized to permit liquid, but not solids, to pass through. In some cases, third valve is positioned at the upstream end of the primary influent pipe. In some cases, the excreta sample capture device further includes a fourth valve positioned at the upstream end of the primary influent pipe; and a tertiary influent pipe positioned underneath the fourth valve.

In some cases, the sample extraction vessel includes heating or freezing elements. In some cases, the sample extraction vessel includes a substrate-based processing system. In some cases, the sample extraction vessel includes a liquid-based processing system.

In some cases, the excreta sample capture device further includes at least one of an optical sensor, a gas sensor, an acoustic sensor, or a thermal sensor in the primary influent pipe and/or sample extraction vessel. In some cases, the excreta sample capture device further includes at least one of a storage device or transceiver coupled to one or more of the sensors in the primary influent pipe and/or sample extraction vessel or coupled to a processing system.

In some cases, the excreta sample capture device further includes a controller. In some cases, the controller is configured to direct operation of the at least one of the optical sensor, the gas sensor, the acoustic sensor, or the thermal sensor. In some cases, the controller is configured to receive data from the at least one of the optical sensor, the gas sensor, the acoustic sensor, or the thermal sensor. In some cases, the excreta sample capture device further includes one or more storage media having instructions stored thereon that when executed by the controller, direct the controller to at least: initiate closing of the first valve; open the second valve; and capture a sample of the excreta contained within influent. In some cases, the excreta sample capture device further includes an optical imaging sensor or a camera, and the instructions that direct the controller to capture the sample of the excreta contained within the influent includes capturing, via the optical imaging sensor or the camera, an image of the excreta contained within the influent.

In some cases, the instructions that direct the controller further include receiving an indication that the influent is being received in the upstream end of the primary influent pipe. In some cases, the excreta sample capture device further includes a sensor located upstream of the second valve, and the instructions that direct the controller to receive the indication that the influent is being received in the upstream end of the primary influent pipe includes receiving, via the sensor, an indication that the influent containing the excreta is being received in the primary influent pipe. In some cases, the instructions that direct the controller further include determining, from the indication received via the sensor, a consistency of the excreta. In some cases, the sensor is a turbidity sensor. In some cases, the instructions that direct the controller further include providing, via the spray jet, a jet of liquid across any excreta remaining from the influent to cause liquification of at least some of that excreta. In some cases, the instructions that direct the controller to capture the sample of the excreta contained within the influent includes collecting, via the sample extraction vessel, the sample of the excreta that is liquified by the jet of liquid.

A method of using an excreta sample capture device includes receiving influent in a primary influent pipe; initiating a closing of a first valve positioned at a downstream end of a primary influent pipe; opening a second valve positioned underneath and between an upstream end of the primary influent pipe and the downstream end of the primary influent pipe; and capturing a sample of the excreta contained within the influent.

In some cases, the capturing of the sample of the excreta contained within the influent includes capturing, via an optical imaging sensor or camera, an image of the excreta contained within the influent. In some cases, the method further includes providing, via a spray jet positioned above the second valve, a jet of liquid across any excreta remaining from the influent to cause liquification of at least some of the excreta. In some cases, the capturing the sample of the excreta contained within the influent includes collecting, via a sample extraction vessel located downstream from the second valve, the sample of the excreta that is liquified by the jet of liquid.

In some cases, initiating the closing of the first valve includes partially closing the first valve. In some cases, initiating the closing of the first valve includes fully closing the first valve. In some cases, the method further includes opening a third valve positioned upstream of the first valve until liquid from the influent has been drained from the primary influent pipe; and closing the third valve. In some cases, the third valve is radially adjacent to the second valve. In some cases, the third valve is positioned at the upstream end of the primary influent pipe. In some cases, opening the third valve until the liquid from the influent has been drained from the primary influent pipe further includes simultaneously opening a fourth valve positioned at the upstream end of the primary influent pipe, and wherein closing the third valve further includes closing the fourth valve. In some cases, the method further includes closing the second valve; opening the first valve; and providing a sufficient amount of water to flush any remaining excreta downstream of the first valve.

In some cases, the method further includes capturing an image of the influent in response to receiving influent in the upstream end of the primary influent pipe. In some cases, the method further includes determining, from the captured image of the influent, a Bristol scale value of the excreta within the influent; and adjusting, based on the determined Bristol scale value of the excreta within the influent, a pressure of the jet of liquid provided via the spray jet positioned above the second valve. In some cases when the determined Bristol scale value of the excreta within the influent is seven, the pressure of the jet of liquid provided via the spray jet is adjusted to zero.

In some cases, the method further includes receiving, via a sensor located upstream of the second valve, an indication that the influent is being received in the primary influent pipe. In some cases, the method further includes determining, from the indication that the influent is being received in the primary influent pipe, a consistency of the excreta contained within the influent. In some cases, the opening of the second valve is performed in response to liquid from the influent being drained from the primary influent pipe.

One or more storage media having instructions stored thereon that when executed by a controller, direct the controller to at least initiate a closing of a first valve positioned at a downstream end of a primary influent pipe; open a second valve positioned underneath and between an upstream end of the primary influent pipe and the downstream end of the primary influent pipe; provide, via a spray jet positioned above the second valve, a jet of liquid across any excreta remaining from the influent to cause liquification of at least some of that excreta; and collect, via a sample extraction vessel located downstream from the second valve, a sample of the excreta that is liquified by the jet of liquid.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Excreta sampling toilet and inline specimen analysis systems and methods are provided. An excreta sample capture device as described herein provides a way to get the valuable health and wellness information for individuals and populations of people without requiring any handling of the excreta by the user. Advantageously, users may simply flush the toilet (as they normally would when using the restroom) and their excreta is automatically captured and available for analysis. The resulting analysis can provide individualized and/or community data on users' health and well-being. Indeed, the automated capture of excreta samples can provide individuals and the public with all of the benefits of using excreta samples for diagnosis and evaluation of treatment regimens, as well as the benefit of information that is not normally obtained from excreta samples such as information gleaned from uniform optical imaging and/or gas detection.

As used herein, capturing a sample of excreta includes capture of data via sensors, cameras, tests, and/or other known diagnostic tools, as well as collection of a physical sample of that excreta for further testing/analysis.

Figure 1A:
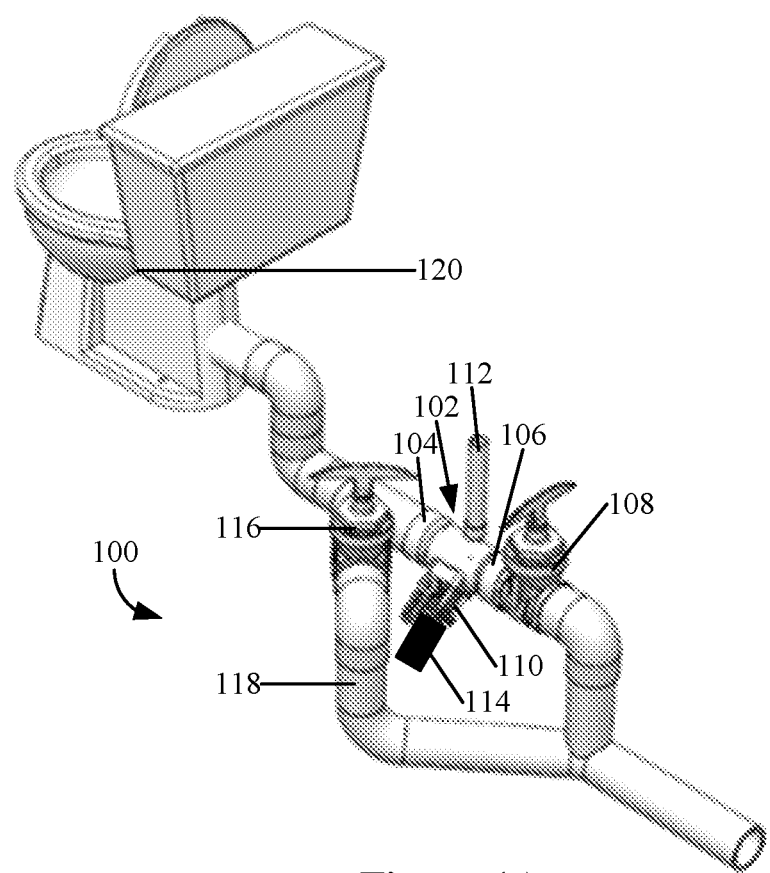
FIG. 1A illustrates an angled view of an excreta sample capture device attached to a toilet.
Figure 1B:
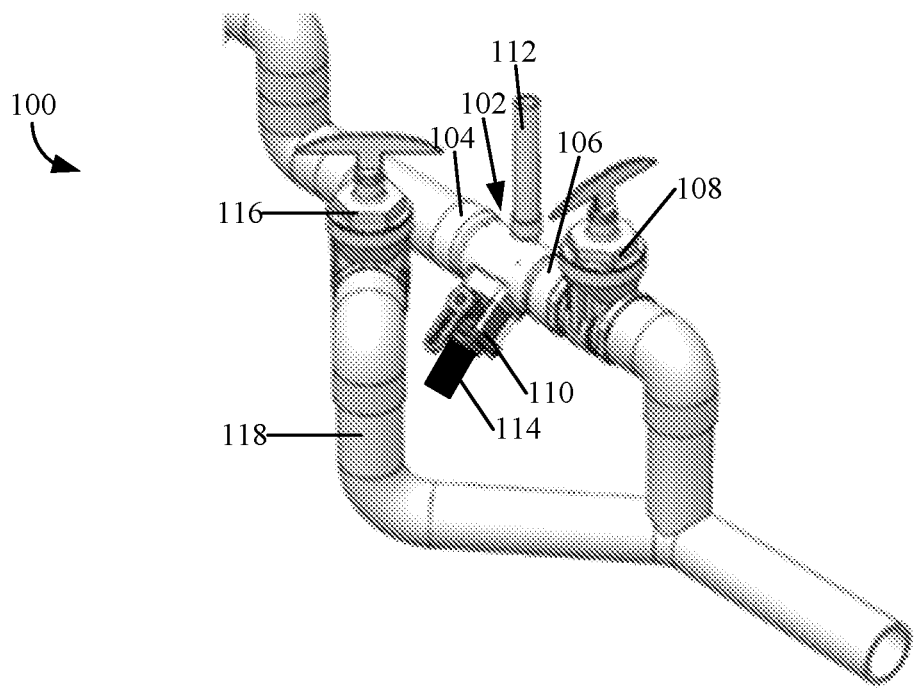
FIG. 1B illustrates a close-up of the angled view of the excreta sample capture device of FIG. 1A.

FIG. 1A illustrates an angled view of an excreta sample capture device attached to a toilet. FIG. 1B illustrates a close-up of the angled view of the excreta sample capture device of FIG. 1A. Referring to FIGS. 1A and 1B, an excreta sample capture device 100 includes a primary influent pipe 102 that receives influent from a toilet(s) 120 and includes an upstream end 104 and a downstream end 106. The excreta sample capture device 100 also includes a first valve 108 positioned at the downstream end 106 of the primary influent pipe 102, a second valve 110 positioned between the upstream end 104 and the downstream end 106 of the primary influent pipe 102, a spray jet 112 positioned above the second valve 110 and a sample extraction vessel 114 located downstream of the second valve 110.

In some cases, the excreta sample capture device 100 includes a third valve (not shown in these figures) positioned between the upstream end 104 of the primary influent pipe 102 and the downstream end 106 of the primary influent pipe 102 and a secondary influent pipe (not shown in these figures) positioned underneath the third valve. In some cases, the secondary influent pipe is sized to permit liquid, but not solids, to pass through. In some cases, the third valve is radially adjacent to the second valve 110. In some cases, the secondary influent pipe may bifurcate from the plumbing system from the primary influent pipe 102 and then rejoin/reconnect to the plumbing system downstream of the first valve 108.

In some cases, the excreta sample capture device includes a fourth valve 116 positioned at the upstream end 104 of the primary influent pipe 102. In some cases, a tertiary influent pipe 118 is positioned underneath the fourth valve 116. In some cases, the tertiary influent pipe 118 is sized to permit liquids and solids to pass through. In some cases, the tertiary influent pipe 118 bypasses the primary influent pipe 102. In other words, the tertiary influent pipe 118 may bifurcate from the plumbing system/piping upstream of the primary influent pipe 102 and then rejoin/reconnect to the plumbing system/piping downstream of the first valve 108. In some cases, the excreta sample capture device 100 is placed downstream of the P-trap or S-trap that is placed on most toilets to prevent noxious gases from rising up through the toilet to the bathroom. Advantageously, smell/odor is not increased by the use of the excreta sample capture device 100.

FIGS. 2A-2D illustrate cross-sectional views of an excreta sample capture device as an excreta sample is captured. FIGS. 3A and 3B illustrate flowcharts of example operations performed by an excreta sample capture device such as illustrated in FIGS. 2A-2D. Referring to FIGS. 2A-2C and FIG. 3A, a method 300 of using an excreta sample capture device 200 includes receiving (302) influent 208 in the primary influent pipe 206, initiating (304) a closing of a first valve 202 positioned at a downstream end 204 of a primary influent pipe 206, opening (306) a second valve 210 positioned underneath and between an upstream end 212 of the primary influent pipe 206 and the downstream end 204 of the primary influent pipe 206, and capturing (310) a sample 222 of the excreta 218 that is contained in the influent 208.

In some cases, the method 300 further includes providing (308), via a spray jet 214 positioned above the second valve 210, a jet of liquid 216 across any excreta 218 remaining from the influent 208 to cause liquification of at least some of that excreta 218. In some cases, the capturing (310) of the sample 222 of the excreta 218 that is contained in the influent includes collecting, via a sample extraction vessel 220 located downstream from the second valve 210, the sample 222 of the excreta 218 that is liquified by the jet of liquid 216. In some cases, the capturing (310) of the sample 222 of the excreta 218 that is contained in the influent includes capturing, via an optical imaging sensor and/or camera, an image of the excreta 218 contained within the influent 208. It should be understood that, even though a spray jet 214 is illustrated in the embodiment shown in FIGS. 2A-2D, the spray jet 214 may be omitted and/or not used in certain implementations. For example, in some cases, the capture of the sample 222 of the excreta 218 includes capturing the image of the excreta 218 contained within the influent 208 (and/or other measurements taken via sensors) but does not include collection (and retainment) of a physical sample 222 of feces from the excreta 218. Accordingly, in certain implementations, the sample extraction vessel 220 can also be omitted.

In some cases, initiating (304) the closing of the first valve 202 includes partially closing the first valve 202, such that liquid, but not solid excreta 218, may pass through the first valve 202. In some cases, the opening (306) of the second valve 210 is performed in response to liquid 224 from the influent 208 being drained from the primary influent pipe 206, as described in further detail with respect to FIG. 7. It should be understood that as used herein, excreta sample collection generally refers to feces sample collection. Indeed, existing urine collection toilets that collect urine before the urine is mixed with water/liquid in the toilet may be used in conjunction with the excreta sample capture device 200. However, as will become apparent below, both liquid and solid feces may be collected by an excreta sample capture device.

Figure 2A:
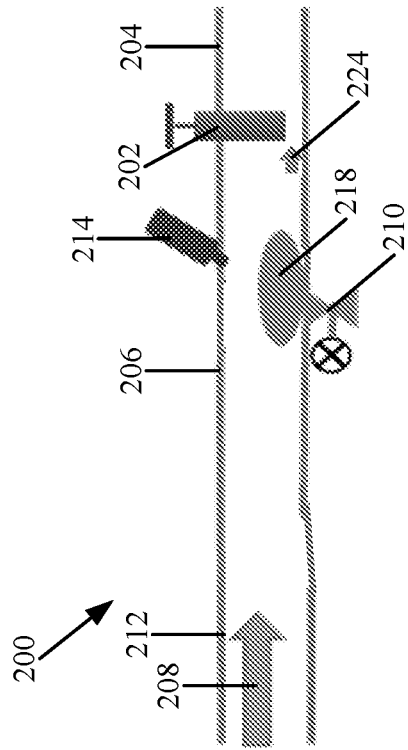
FIGS. 2A-2D illustrate cross-sectional views of an excreta sample capture device as an excreta sample is captured.
Figure 2C:
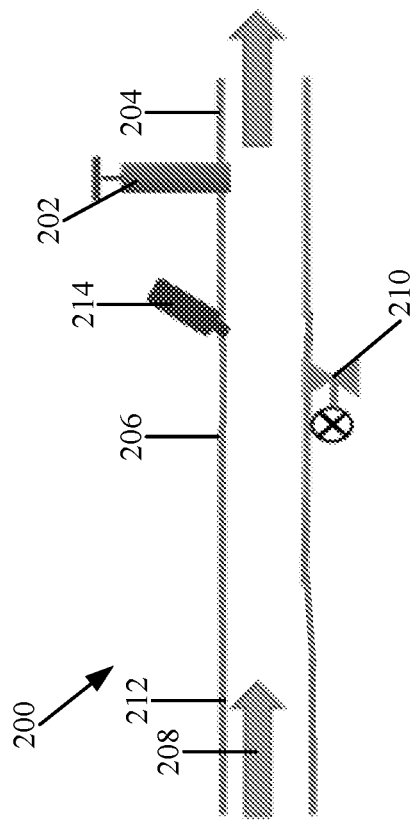
Figure 2B:
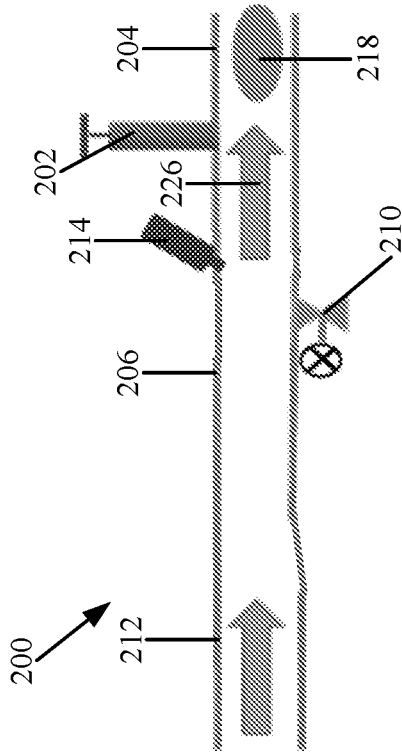
Figure 2D:
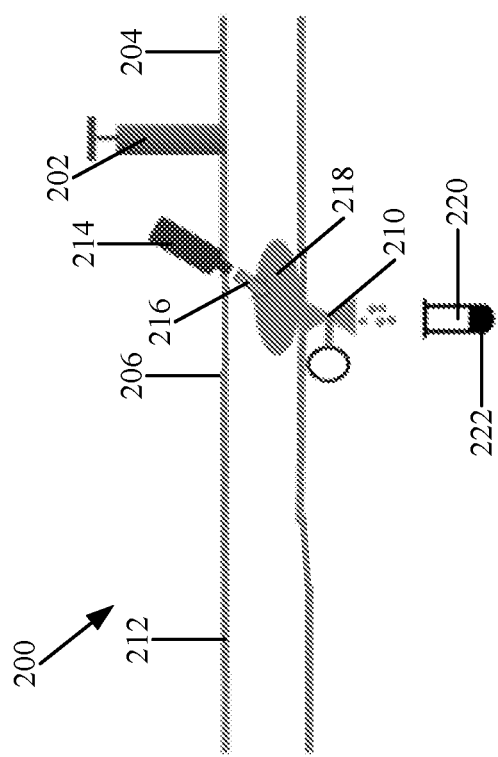
Figure 3A:
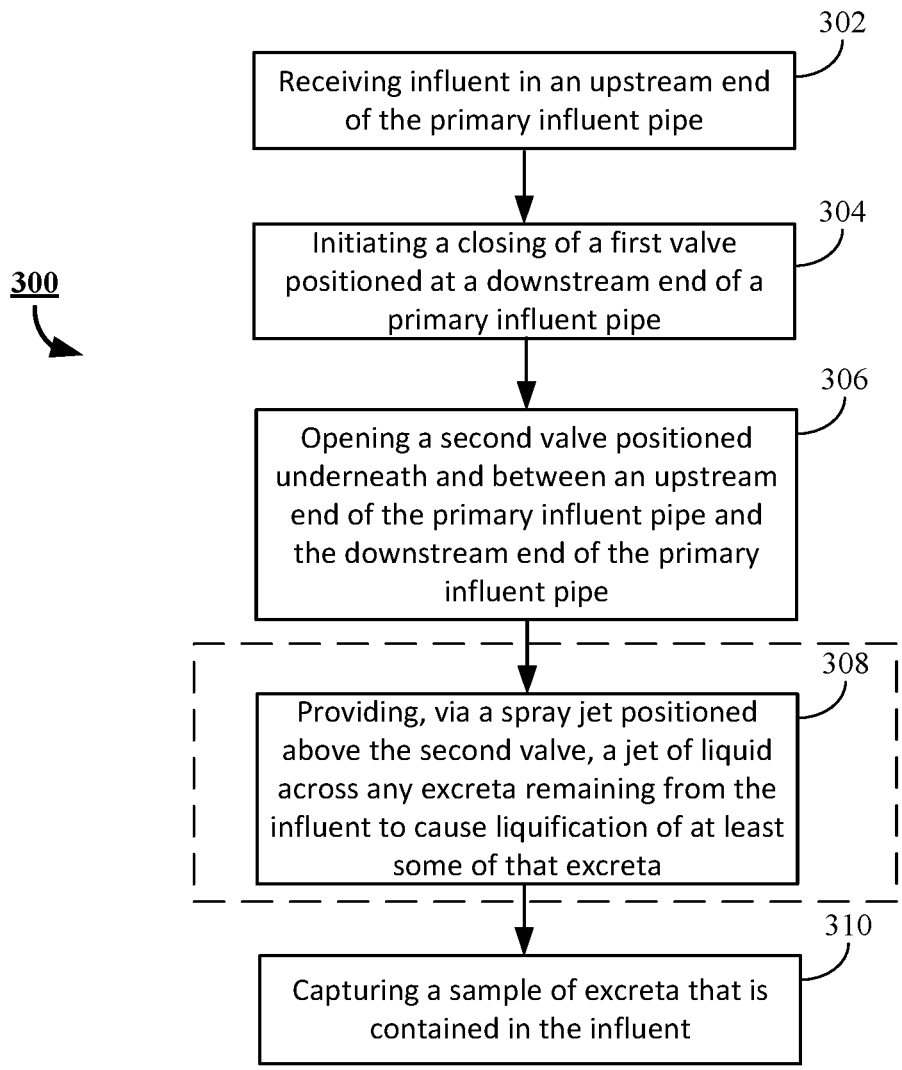
FIGS. 3A and 3B illustrate flowcharts of example operations performed by an excreta sample capture device such as illustrated in FIGS. 2A-2D.
Figure 3B:
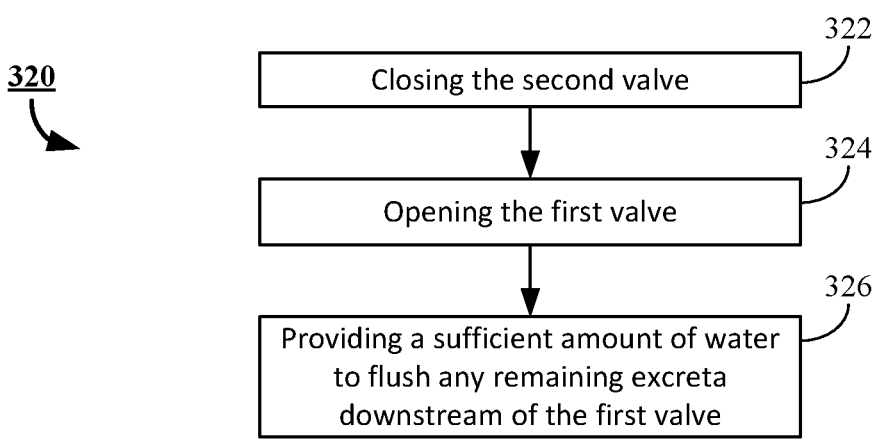

Referring to FIGS. 2D and 3B, a method 320 of clearing the primary influent pipe 206 includes closing (322) the second valve 210, opening (324) the first valve 202, and providing (326) a sufficient amount of water 226 to flush any remaining excreta 218 downstream of the first valve 202. In some cases, after providing (326) the sufficient amount of water 226 to flush any remaining excreta 218 downstream of the first valve 202, a second spray jet (not shown) may provide a cleaning solution to the primary influent pipe 206. In some cases, a sufficient amount of water to rinse the cleaning solution from the primary influent pipe 206 may be subsequently provided.

FIGS. 4A-4D illustrate cross-sectional views of an excreta sample capture device as an excreta sample is captured. FIGS. 5A and 5B illustrate flowcharts of example operations performed by an excreta sample capture device such as illustrated in FIGS. 4A-4D. Referring to FIGS. 4A-4C and FIG. 5A, a method 500 of using an excreta sample capture device 400 includes receiving (502) influent 408 in the primary influent pipe 406, closing (504) of a first valve 402 positioned at a downstream end 404 of a primary influent pipe 406, opening (506) a third valve 410 positioned between an upstream end 412 of the primary influent pipe 406 and the downstream end 404 of the primary influent pipe 406 and a fourth valve 414 positioned at the upstream end 412 of the primary influent pipe 406 until liquid 416 from the influent 408 has been drained from the primary influent pipe 406, closing (508) the third valve 410 and the fourth valve 414, opening (510) a second valve 418 positioned underneath the primary influent pipe 406 and radially adjacent to the third valve 410, providing (512), via a spray jet 420 positioned above the second valve 418, a jet of liquid 422 across any excreta 424 remaining from the influent 408 to cause liquification of at least some of that excreta 424, and collecting (514), via a sample extraction vessel 426 located downstream from the second valve 418, a sample 428 of the excreta 424 that is liquified by the jet of liquid 422.

In some cases, a username and/or biometric input may be received prior to a user using the excreta sample capture device 400. In some cases, the closing (504) of the first valve 402 positioned at the downstream end 404 of the primary influent pipe 406 is performed in response to an indication that excreta is (possibly) included with the influent 408. In some cases, this indication is from a flush of a toilet. In some cases, this indication is from a detection (e.g., via sensors located upstream of the primary influent pipe 406, as described in 7). In some cases, this indication is from input of a username or some biometric that is received prior to a user using the excreta sample capture device 400. In some cases, sensors may also detect what the consistency of the excreta is (e.g., whether excreta is liquid or solid). In cases where all liquid excreta is detected, certain steps in the method 500 may not be performed (e.g., opening (506) and closing (508) the third valve 410 and the fourth valve 414) so that the excreta 424 sample can still be collected.

In some cases, the opening (506) the third valve 410 and the fourth valve 414 until liquid 416 from the influent 408 has been drained from the primary influent pipe 406 includes opening the third valve 410 and the fourth valve 414 for a predetermined period of time. For example, by knowing the configuration (e.g., size and position) and material (e.g., the resistance coefficient) of each valve 410, 414 and the pipes downstream of those valves, as well as the (approximate) amount of influent 408 being received in the primary influent pipe 406 the predetermined period of time can be determined. In some cases, the size of the third valve 410 (and downstream piping until it is rejoined/reconnected to the main sewer line) is one inch or less. In some cases, the piping used in the excreta sample capture device 400 is PVC. In some cases, the opening (506) the third valve 410 and the fourth valve 414 until liquid 416 from the influent 408 has been drained from the primary influent pipe 406 is performed in response to an indication (e.g., via one of the sensors described in FIG. 7) that liquid 416 from the influent 408 remains in the primary influent pipe 406. In some cases, the closing (508) the third valve 410 and the fourth valve 414 is performed after the predetermined period of time. In some cases, the closing (508) the third valve 410 and the fourth valve 414 is performed in response to an indication (e.g., via one of the sensors described in FIG. 7) that no liquid 416 (or just a small amount of the liquid 416) from the influent 408 remains in the primary influent pipe 406.

In some cases, opening (510) the second valve 418 is performed in response to closing (508) the third valve 410 and the fourth valve 414. In some cases, the opening (510) of the second valve 418 is performed in response to liquid 416 from the influent 408 being drained from the primary influent pipe 406; and the draining of the liquid 416 may be detected from one of the described with respect to FIG. 7. In some cases, providing (512), via the spray jet 420, the jet of liquid 422 across any excreta 424 remaining from the influent 408 to cause liquification of at least some of that excreta 424 is performed in response to opening (510) the second valve 418. In some cases, providing (512), via the spray jet 420, the jet of liquid 422 across any excreta 424 remaining from the influent 408 to cause liquification of at least some of that excreta 424 is performed for a predetermined period of time. In some cases, providing (512), via the spray jet 420, the jet of liquid 422 across any excreta 424 remaining from the influent 408 to cause liquification of at least some of that excreta 424 is performed until a large enough sample 428 of liquified excreta has been collected (516) for the needs of the testing being performed. Determining that a large enough sample 428 of liquified excreta has been collected (516) for the needs of the testing being performed may include using or more sensors (e.g., as described in FIG. 7) in the primary influent pipe 406 or a sensor (e.g., a laser sensor or pressure sensor) positioned in/around the sample extraction vessel 426.

In some cases, the jet of liquid 422 may be a buffer solution that is used for mixing with an excreta sample. In some cases, only one of the third valve 410 and the fourth valve 414 may be implemented in an excreta sample capture device 400. In some cases, the aperture 432 may be filled with various sensors (e.g., a pressure sensor, a optical sensor/camera, a gas sensor, a turbidity sensor, or an acoustic transducer/receiver), which is explained in further detail with respect to FIG. 7. In some cases, one of those sensors is an optical sensor/camera, which can be used to capture an image of the influent 408/excreta 424. This image can be taken in response to receiving (502) the influent 408 in the primary influent pipe 406. The image can then be used to determine a Bristol scale value of the excreta 424 within the influent 408 and adjust, based on the determined Bristol scale value of the excreta 424 within the influent 408, a pressure of the jet of liquid 422 provided via the spray jet 420. In some cases, when the determined Bristol scale value of the excreta 424 within the influent 408 is seven (e.g., loose/liquid), the pressure of the jet of liquid 422 provided via the spray jet 420 is adjusted to zero. In other words, the spray jet 420 may not be used in cases where the Bristol scale value of the excreta 424 within the influent 408 is seven.

Figure 4A:
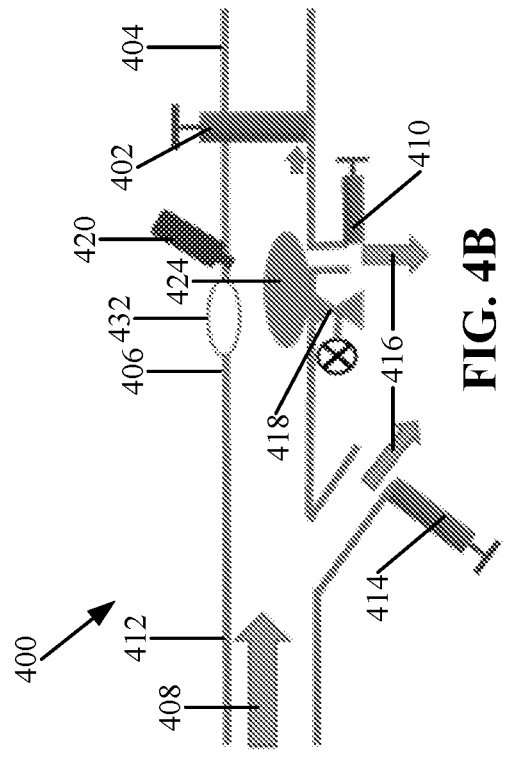
FIGS. 4A-4D illustrate cross-sectional views of an excreta sample capture device as an excreta sample is captured.
Figure 4B:
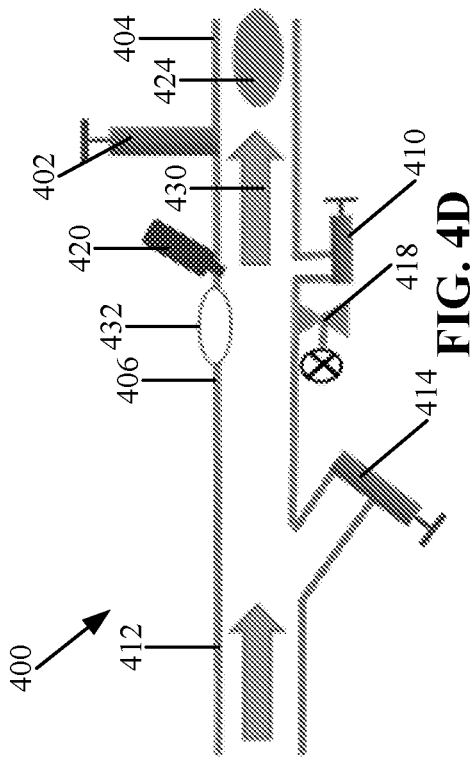
Figure 4C:
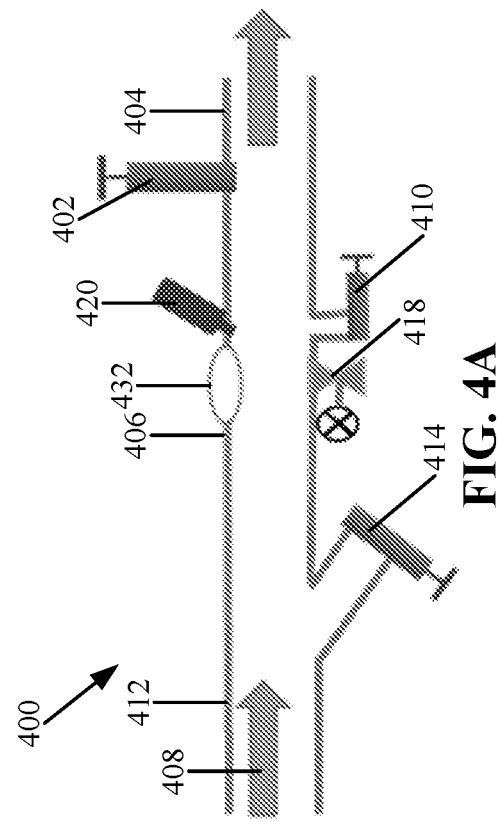
Figure 4D:
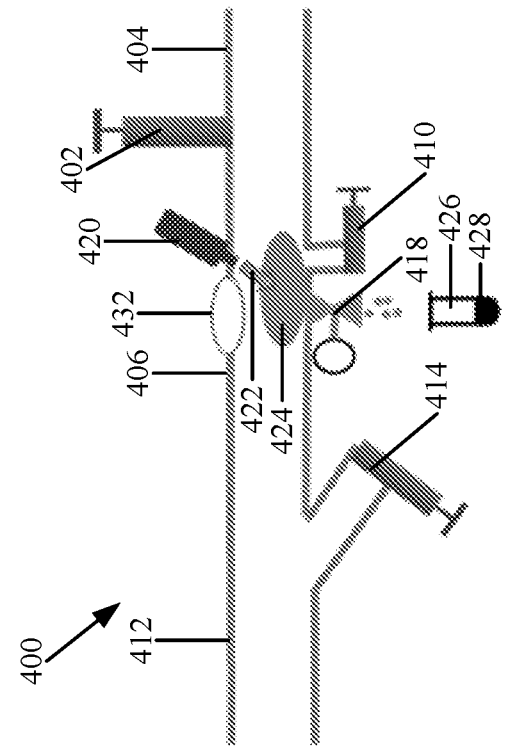
Figure 5A:
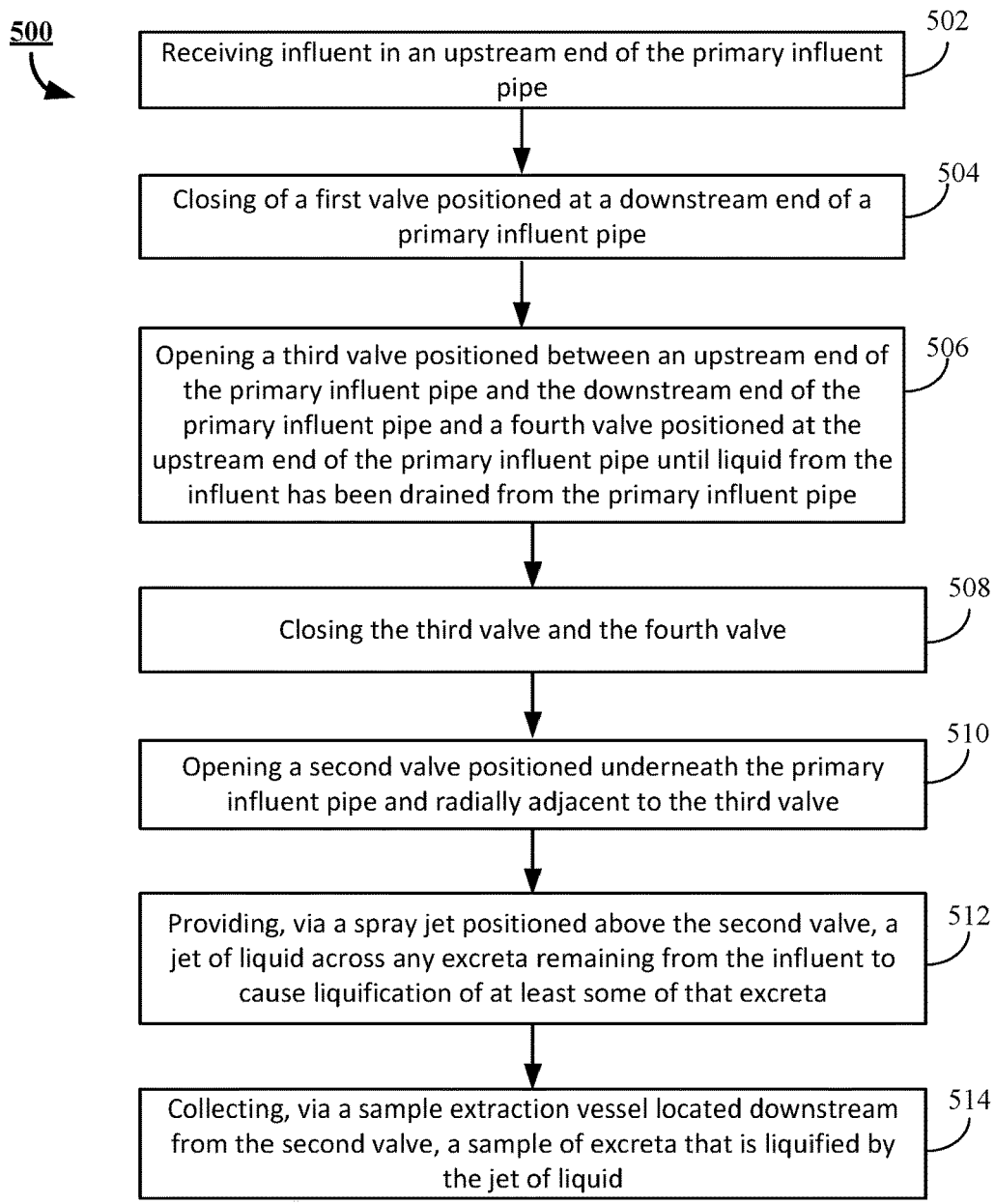
FIGS. 5A and 5B illustrate flowcharts of example operations performed by an excreta sample capture device such as illustrated in FIGS. 4A-4D.
Figure 5B:
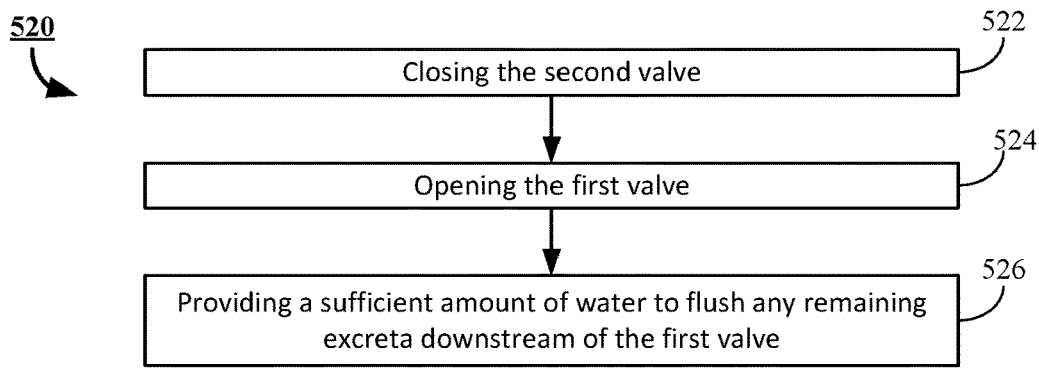

Referring to FIGS. 4D and 5B, a method 520 of clearing the primary influent pipe 406 includes closing (522) the second valve 418, opening (524) the first valve 402, and providing (526) a sufficient amount of water 430 to flush any remaining excreta 424 downstream of the first valve 402. In some cases, after providing (526) the sufficient amount of water 430 to flush any remaining excreta 424 downstream of the first valve 402, a second spray jet (not shown) may provide a cleaning solution to the primary influent pipe 406. In some cases, a sufficient amount of water to rinse the cleaning solution from the primary influent pipe 406 may be subsequently provided.

It should be understood that the valves described herein may be any type of valve that permits the described functionality for that valve, including but not limited to, a gate valve, a globe valve, a check valve, a plug valve, a ball valve, a butterfly valve, a needle valve, a pinch valve, a pressure relief valve, a knife valve, a pinch valve, a solenoid valve, and/or an inflatable bladder.

Figure 6B:
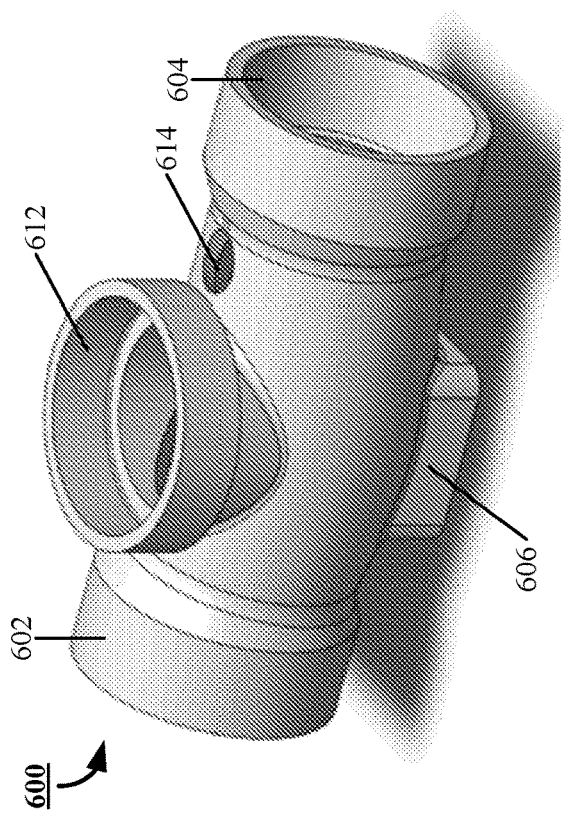
FIGS. 6A and 6B illustrate a side view and an angled view, respectively, of a primary influent pipe of an excreta sample capture device.
Figure 6A:
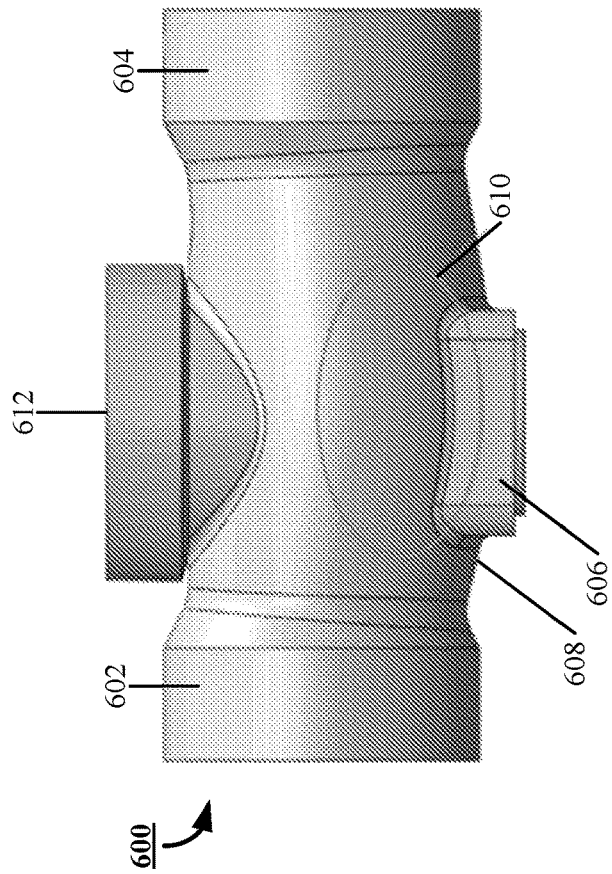

FIGS. 6A and 6B illustrate a side view and an angled view, respectively, of a primary influent pipe of an excreta sample capture device. Referring to FIGS. 6A and 6B, a primary influent pipe 600 receives influent from a toilet(s) and includes an upstream end 602 and a downstream end 604. In other words, influent flows from the upstream end 602 of the primary influent pipe 600 to the downstream end 604 of the primary influent pipe 600. The primary influent pipe 600 also includes a sampling port 606 for receiving an excreta sample. In some cases, a valve (e.g., second valve 110 of FIGS. 1A and 1B, second valve 210 of FIGS. 2A-2D, of second valve 418 of FIGS. 4A-4D) is included so that the excreta sample is received via the open valve at the correct time in the excreta sample capture process (e.g., steps 306, 308, and 310 of FIG. 3A or 510, 512, and 514 of FIG. 5A).

As illustrated in FIG. 6A, in some cases, the primary influent pipe 600 may be longitudinally curved on a bottom surface 608 to provide gravitational assistance for capturing/collecting the excreta sample. The longitudinally curved bottom surface 608 of the primary influent pipe 600 can also encourage immobilization of the excreta (e.g., via gravity), in what is referred to as an immobilization area 610, prior to excreta sample capture. In other words, the lowest point of the longitudinally curved bottom surface 608 of the primary influent pipe 600 can be at the sampling port 606.

The primary influent pipe 600 further includes an imaging port 612 for placement of an optical sensor/camera, which can be used to capture an image of the influent/excreta. In some cases, the imaging port 612 is placed vertically above the sampling port 606. In some cases, the imaging port 612 may also include space for placement of other sensors, including, but not limited to a gas sensor, a turbidity sensor, a pressure sensor, and/or an acoustic transducer/receiver (described in more detail with respect to FIG. 7). In some cases, these sensors may be added in and/or around the immobilization area 610/sampling port 606 instead of directly within the imaging port 612. The primary influent pipe 600 further includes a spray jet aperture 614 for placement of a spray jet (e.g., spray jet 112 of FIGS. 1A and 1B, spray jet 214 of FIGS. 2A-2D, and/or spray jet 420 of FIGS. 4A-4D. In some cases, the spray jet aperture 614 may provide space for two spray jets (e.g., a spray jet for providing a buffer solution to cause liquification of the excreta and a spray jet for providing a cleaning solution to disinfect the primary influent pipe 600).

Figure 7:
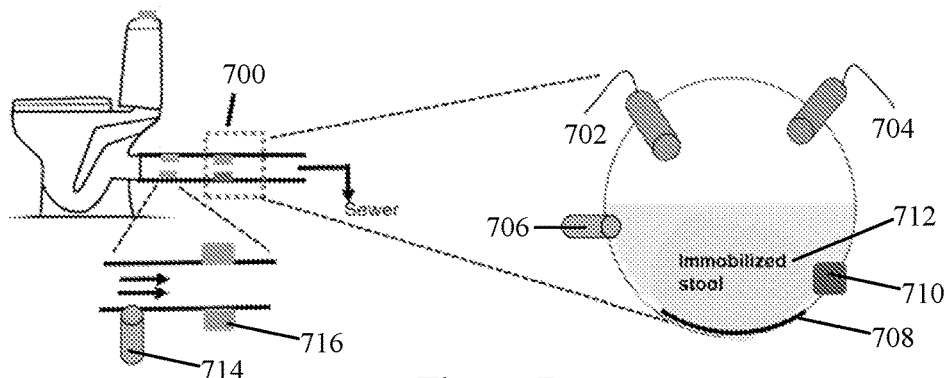
FIG. 7 illustrates an example of various sensors that may be incorporated into an excreta sample capture device.

FIG. 7 illustrates an example of various sensors that may be incorporated into an excreta sample capture device. Referring to FIG. 7, an excreta sample capture device 700 can include an optical imaging/camera sensor 702, a gas sensor 704, a turbidity sensor 706, a pressure sensor 708, and/or an acoustic transducer/receiver 710. In some cases, an excreta sample capture device 700 can include at least one of a storage device or transceiver coupled to one of the sensors 702, 704, 706, 708, 710 (e.g., for storing and/or sending measurements taken by the sensors). The optical imaging/camera sensor 702 may be used to take images of the influent/excreta 712. Furthermore, due to the consistent light conditions (e.g., the inside of a primary influent pipe is dark save for any light emitted from the optical imaging/camera sensor 702), images can be used to consistently determine color, shape, and size of the excreta 712. The gas sensor 704 can be used to detect the presence of certain gases (e.g., methane) that often accompany excreta 712. The gas sensor 704 can also be used to detect the percentage of certain gases, which can also be relevant to an individual's gastrointestinal health. The turbidity sensor 706 can be used to determine the consistency (e.g., loose/liquid versus normal/solid) of the excreta 712, as well as the presence of other materials in the influent (e.g., urine and/or toilet paper). It should be understood that, for example, toilet paper generally does not interfere with most excreta testing due to the relatively inert nature of toilet paper. A pressure sensor 708 can be used to determine the weight and/or mass of the excreta 712 in the influent. For instance, by knowing how much water is normally captured in an empty flush, the pressure created by that water can be subtracted/discounted, leaving the weight of excreta 712. For instance, the weight of toilet paper may be subtracted/discounted through detection of its presence via other sensors (e.g., optical imaging/camera sensor 702 or turbidity sensor 706); urine may be physically subtracted/discounted from the influent (e.g., via integration of a urine collection toilet), or may also be subtracted/discounted through detection of its presence via other sensors (e.g., optical imaging/camera sensor 702 or turbidity sensor 706). An acoustic sensor 710 may be used to detect the consistency and/or mass of the excreta 712 which can then be used to alter the method of excreta sample capture, as described with respect to method 500. In some cases, the acoustic sensor 710 is an acoustic transducer/receiver. In some cases, the acoustic transducer/receiver 710 is an ultrasound transducer/receiver 710.

In some cases, a turbidity sensor 714 and/or a laser transmission sensor 716 may be implemented upstream of the sample capture area of the excreta sample capture device 700. For example, the turbidity sensor 714 may be used in addition to or in lieu of turbidity sensor 706. In some cases, the turbidity sensor 714 may be used to determine whether the excreta sample capture device 700 is initiated (e.g., in cases where only urine and/or no excreta 712 is flushed, the excreta sample capture device 700 may not initiate capture of an excreta 712 sample). However, when excreta 712 is detected the excreta sample capture device 700 may initiate capture of an excreta sample (e.g., via method 300 or method 500). Indeed, the turbidity sensor 714 may send an indication to the controller that influent containing excreta is being (or is about to be) received in the primary influent pipe. The turbidity sensor 714 can also be used to determine consistency of excreta, which can then be used to alter the method of excreta sample capture, as discussed with respect to method 500. In some cases, the consistency of the excreta may be correlated to a Bristol scale value, the value of which may be used as described with respect to FIGS. 4A-4C and 5A. In some cases, other sensors (e.g., optical, and/or acoustic) may be placed implemented upstream of the sample capture area of the excreta sample capture device 700. Indeed, any sensor that is able to detect the presence of solids in liquid may be used. The laser transmission sensor 716 may also be used to detect the presence of excreta 712 to initiate capture of an excreta sample.

Figure 8A:
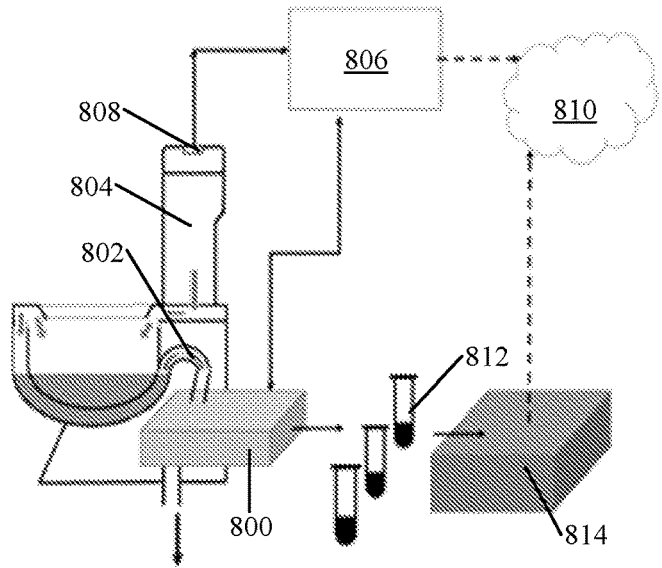
FIGS. 8A and 8B illustrate example operational environments for analysis of excreta specimens and capture of resulting data.
Figure 8B:
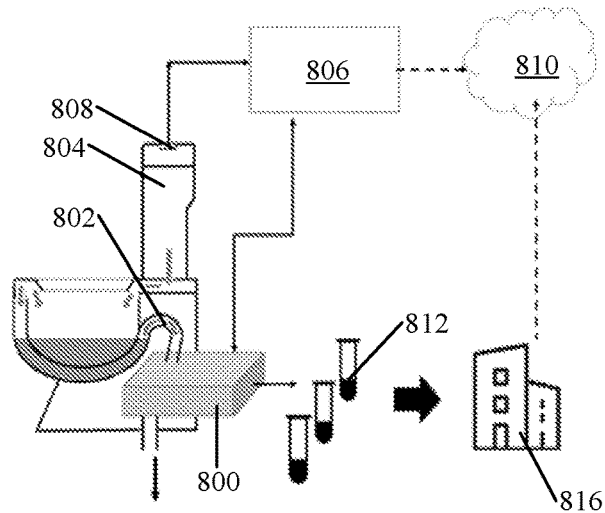

FIGS. 8A and 8B illustrate example operational environments for analysis of excreta specimens and capture of resulting data. Referring to FIGS. 8A and 8B, an excreta sample capture device 800 receives influent 802 from a toilet 804. The operations performed by the excreta sample capture device 800 is controlled by an excreta sample capture device controller 806, and those operations may be initiated by, for example, flushing 808 of the toilet 804 (or in some cases, an indication that the toilet 804 has been flushed). In addition to the control of the operations performed by the excreta sample capture device 800, the excreta sample capture device 800 may send information that is captured by sensors to the excreta sample capture device controller 806. That information can then be sent to a remote data repository 810. In some cases, the excreta sample capture device controller 806 includes the ability to control/direct operation and functionality of the sensors. In other words, the excreta sample capture device controller 806 includes the ability to send instructions to a operate a sensor(s) and/or receive data from a sensor(s).

Upon completion of the operations performed by the excreta sample capture device 800, packaged samples 812 may be collected. In some cases, as shown in FIG. 8A, the samples 812 may be used for onsite analysis 814. In some cases, as shown in FIG. 8B, the samples 812 may be shipped to a central laboratory 816 for analysis. In some cases, some onsite analysis 814 may be performed, while a portion of the samples 812 may be shipped to the central laboratory 816 for analysis. For example, an initial screening may be performed via onsite analysis 814, and, in cases where an abnormal result from the screening is found, the remaining sample 812 may be shipped to the central laboratory 816 for more detailed analysis. In any case, information from analysis (e.g., onsite analysis 814 and/or analysis performed by a central laboratory 816) may also be sent to the remote data repository 810.

Figure 9A:
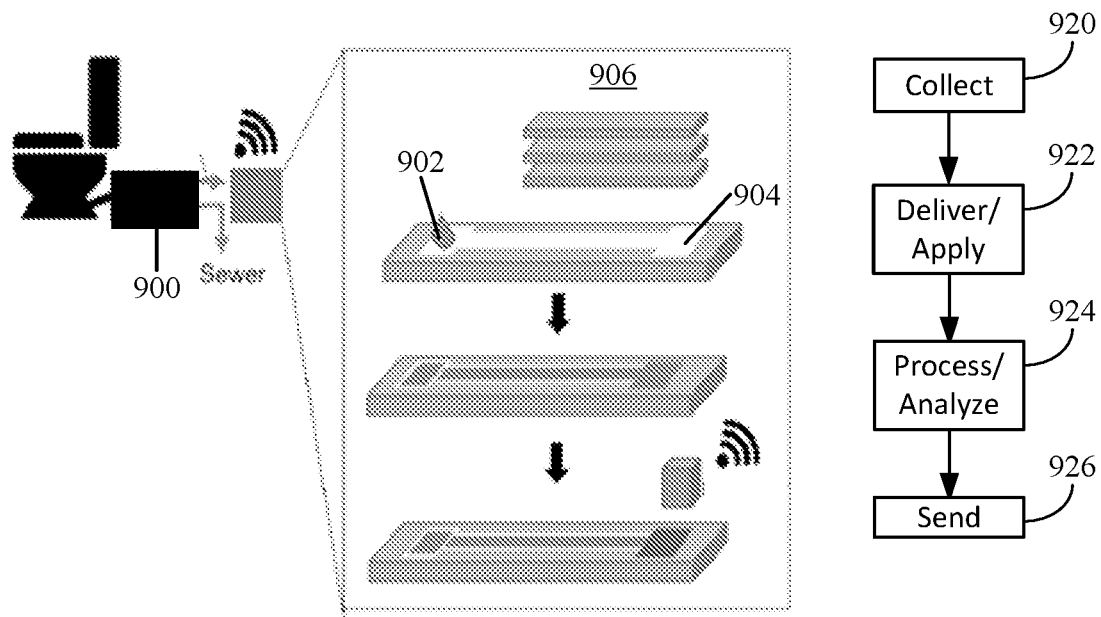
FIGS. 9A and 9B illustrate types of inline diagnostics systems that may be incorporated into an excreta sample capture device.
Figure 9B:
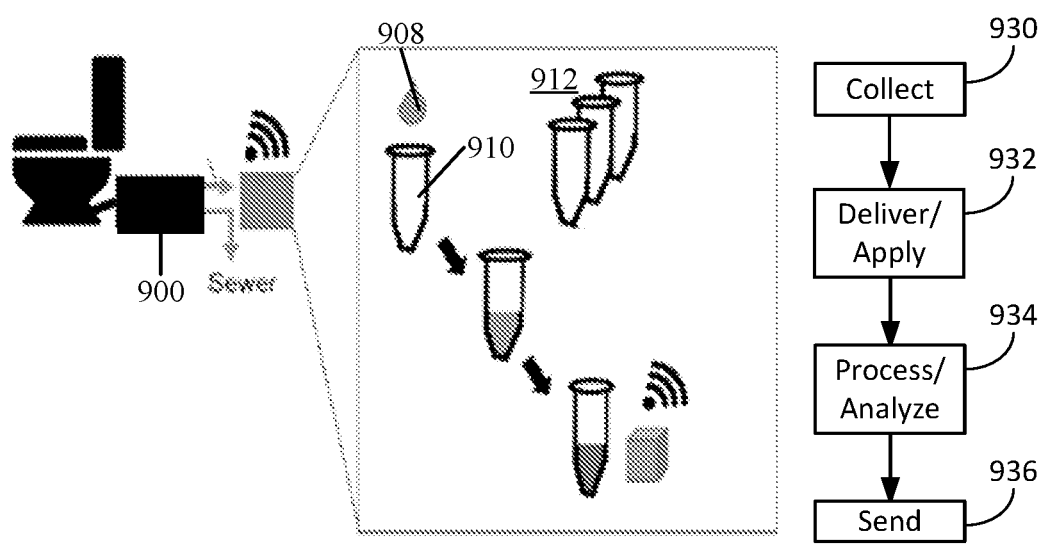

FIGS. 9A and 9B illustrate types of inline diagnostics systems that may be incorporated into an excreta sample capture device. Referring to FIG. 9A, an excreta sample 902 is collected (920) by the excreta sample capture device 900 and then delivered/applied (922) to a card substrate 904 in a paper-based diagnostics system 906. Next, the paper-based diagnostics system 906 processes/analyzes (924) the sample 902. The processing/analysis (924) can include any type of analysis that may be carried out on an excreta sample 902. Once the processing/analysis (924) is completed, the results may be presented via an optical read-out and/or sent (926) to a remote repository (e.g., 810 of FIGS. 8A and 8B).

Referring to FIG. 9B, an excreta sample 908 is collected (930) by the excreta sample capture device 900 and then delivered/applied (932) to a vial 910 in a vial-based diagnostics system 912. Next, the vial-based diagnostics system 912 processes/analyzes (934) the sample 908. The processing/analysis (934) can include any type of analysis that may be carried out on an excreta sample 908. Once the processing/analysis (934) is completed, the results may be presented via an optical read-out and/or sent (936) to a remote repository (e.g., 810 of FIGS. 8A and 8B).

Referring to FIGS. 9A and 9B, in some cases, the card substrate 904/vial 910 includes a dried reagent and/or buffer suitable for excreta sample 902, 908 analysis. In some cases, the processing/analysis 924, 934 includes an amplification step and a low-cost molecular sensing approach as enabled by synthetic biology for sensitive and specific detection. In some cases, an optical read-out 926, 936 is fluorescent for convenience of optical detection inside the paper-based diagnostics system 906/vial-based diagnostics system 912. It should be understood that either system 906, 912 can be configured to accept a wide variety of conventional and/or new substrates/vials. Furthermore, due to the automation of the sample capture and analysis, the system 906, 912 allows for a large volume of samples 902, 908 to be analyzed. In some cases, the system 906, 912 include a cartridge loading door and/or automated feed system for adding the substrates/vials, as well as a receptacle or holding region for storing used samples 902, 908. In some cases, a thermal processing capability (e.g., heating and/or freezing elements) are included in the system 906, 912.

Figure 10A:
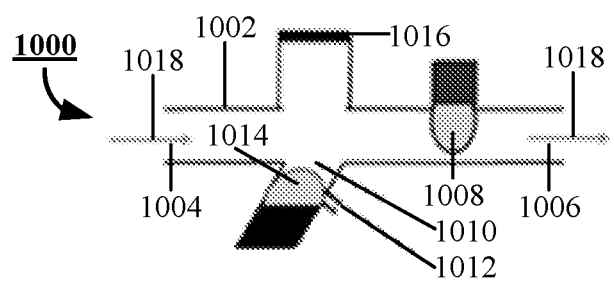
FIGS. 10A-10C illustrate cross-sectional views of an excreta sample capture device as an excreta sample is captured.
Figure 10B:
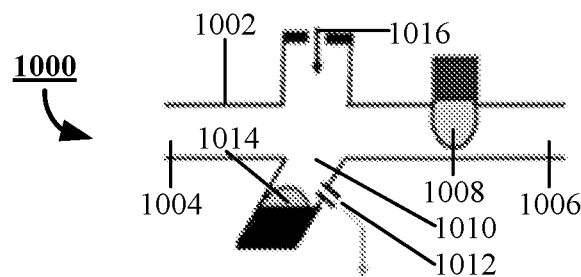
Figure 10C:
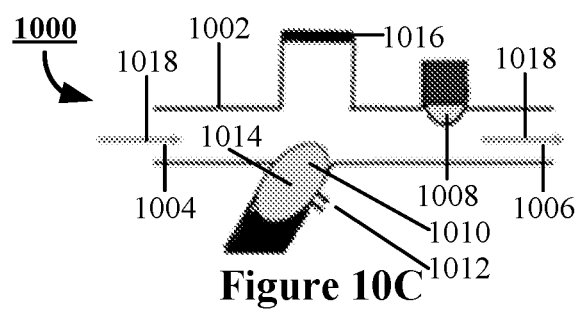

FIGS. 10A-10C illustrate cross-sectional views of an excreta sample capture device as an excreta sample is captured. Referring to FIGS. 10A-10C, an excreta sample capture device 1000 includes a primary influent pipe 1002 having an upstream end 1004 and a downstream end 1006. The excreta sample capture device 1000 further includes a first bladder 1008 positioned at the downstream end 1006 of the primary influent pipe 1002, a sample capture area 1010 positioned between the upstream end 1004 of the primary influent pipe 1002 and the downstream end 1006 of the primary influent pipe 1002, a sample port 1012 positioned adjacent to the sample capture area 1010, a second bladder 1014 positioned within the sample capture area 1010, and a spray jet 1016 positioned above the second bladder 1014/sample capture area 1010. In some cases, the sample capture area 1010 is a pipe that is vertically below the primary influent pipe 1002. In some cases, the second bladder 1014 can be inflated to prevent a sample (e.g., liquified mix of excreta and buffer solution) from reaching the sample port 1012.

Referring to FIG. 10A, influent 1018 may flow into the upstream end of the primary influent pipe 1002 and be stopped by the (inflated) first bladder 1008, allowing any excreta within the influent 1018 to settle within the sample capture area 1010. In some cases, the first bladder 1008, when inflated, only partially closes/seals the primary influent pipe 1002, preventing excreta within the influent 1018 from passing through the primary influent pipe 1002 while allowing the rest of the influent 1018 to pass through the primary influent pipe 1002. The second bladder is also inflated to prevent influent from entering the sample port 1012.

Referring to FIG. 10B, once the excreta from the influent 1018 has settled into the sample capture area 1010, the second bladder 1014 deflates and the spray jet provides a jet of liquid (e.g., excreta buffer solution) across the excreta remaining from the influent 1018 to cause liquification of at least some of that excreta. The now liquified excreta is collected (e.g., via gravity) through the sample port 1012.

Referring to FIG. 10C, the second bladder 1014 is inflated, the first bladder 1008 is deflated, and a sufficient amount of water to flush any remaining excreta through the primary influent pipe 1002 is provided.

FIGS. 11A-11F illustrate cross-sectional views of an excreta sample capture device as an excreta sample is captured. Referring to FIGS. 11A-11F, an excreta sample capture device 1100 includes a primary influent pipe 1102 having an upstream end 1104 and a downstream end 1106. The excreta sample capture device 1100 further includes a bladder 1108 positioned at the downstream end 1106 of the primary influent pipe 1102, a valve 1110 positioned between the upstream end 1104 of the primary influent pipe 1102 and the downstream end 1106 of the primary influent pipe 1102, and a spray jet 1112 positioned above the valve 1110.

Figure 11A:
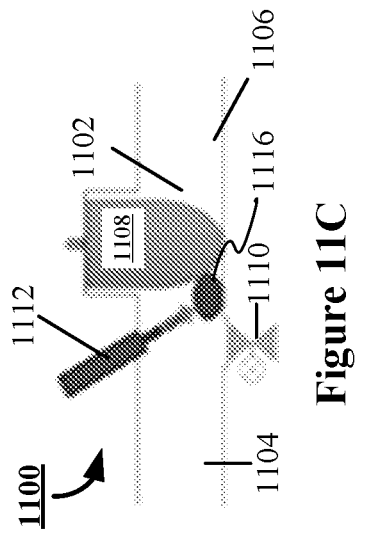
FIGS. 11A-11F illustrate cross-sectional views of an excreta sample capture device as an excreta sample is captured.
Figure 11B:
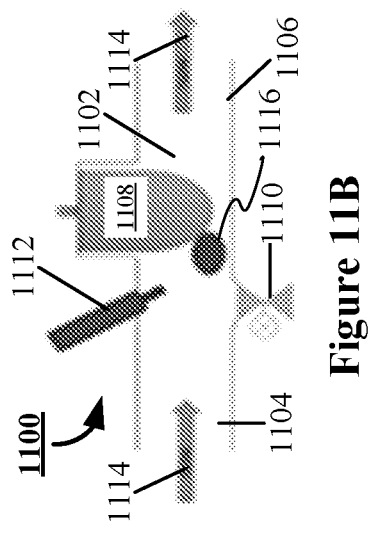
Figure 11C:
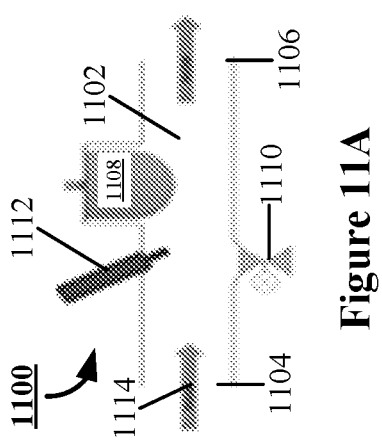

Referring to FIG. 11A, the bladder 1108 is deflated and the valve 1110 is closed, allowing any influent 1114 to pass through the primary influent pipe 1102. Referring to FIG. 11B, the bladder 1108 is partially inflated, allowing liquid in the influent 1114 to pass through the primary influent pipe 1102 while preventing excreta 1116 within the influent 1114 from passing through the primary influent pipe 1102. Referring to FIG. 11C, the bladder 1108 is fully inflated and the spray jet 1112 provides a jet of liquid 1118 (e.g., excreta buffer solution) across the excreta 1116 remaining from the influent 1114 to cause liquification of at least some of that excreta 1116. Furthermore, because the bladder 1108 is fully inflated, the now liquified excreta 1116 is prevented from passing through the primary influent pipe 1102.

Figure 11D:
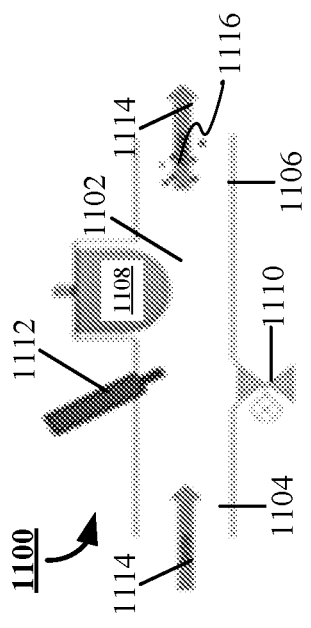
Figure 11E:
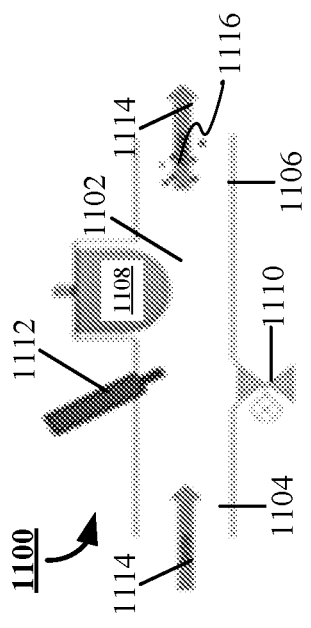
Figure 11F:
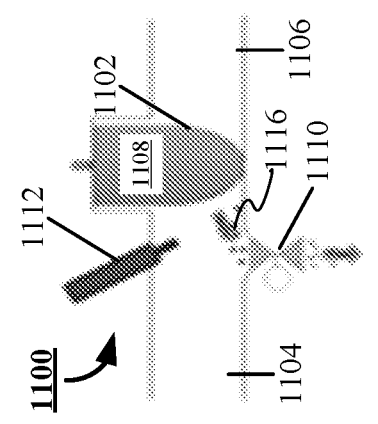

Referring to FIG. 11D, the valve 1110 is opened, allowing the now liquified excreta 1116 to flow through the valve 1110 and into the sample port (not shown in these figures). Referring to FIG. 11E, the valve 1110 is closed. Referring to FIG. 11F, a sufficient amount of water to flush any remaining excreta through the primary influent pipe 1102 is provided.

Figure 12:
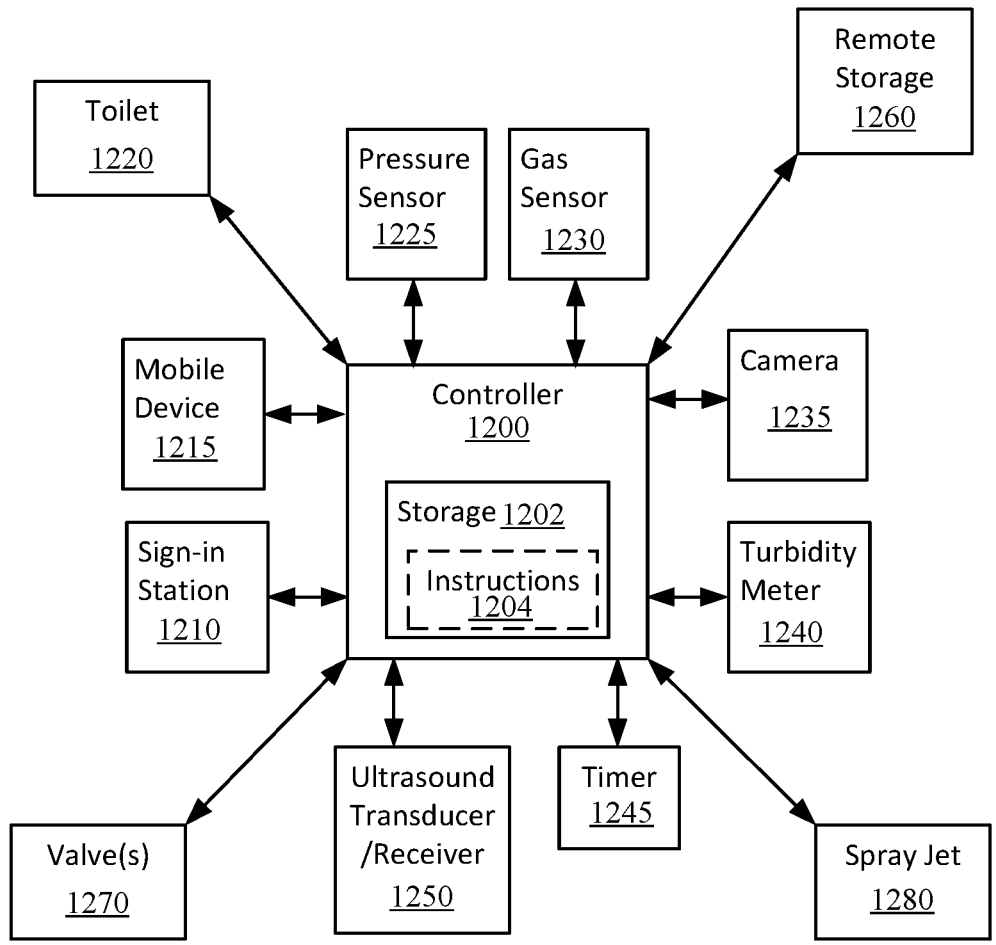
FIG. 12 illustrates an example system architecture for an excreta sample capture device.

FIG. 12 illustrates an example system architecture for an excreta sample capture device. Referring to FIG. 12, a controller 1200 may include storage 1202 having instructions 1204 that are used to carry out the methods described herein (e.g., with respect to processes 300, 320, 500, 520). The controller 1200 can include a variety of communications interfaces enabling the controller 1200 to communicate with a variety of components wired or wirelessly coupled to the controller 1200. The controller 1200 may be in communication with a sign-in station 1210 and/or a mobile device 1215. Both the sign-in station 1210 and/or the mobile device 1215 may be configured to receive a username and/or biometric information from a user so that the results from testing the excreta sample can be associated with that user. The controller 1200 may be in communication with a toilet 1220, pressure sensor 1225, gas sensor 1230, a camera 1235, a turbidity sensor 1240, a timer 1245, and/or an acoustic transducer/receiver 1250 to carry out the methods described herein. The controller may also be in communication with one or valves 1270 and the one or more spray jets 1280 that are described above to carry out the methods described herein. In some cases, the controller 1200 may also be in communication with other sensors that are used to carry out the methods described herein. The controller 1200 may be in communication with a remote storage system 1260 (e.g., on-site, off-site, or cloud-based) to securely send information captured by the excreta sample capture device. In some cases, the communications interfaces can include a network interface for coupling to the Internet or cellular service (e.g., for communicating with a service tied to a mobile application on a mobile device) and/or a short-range interface (near field, wide band, or other common communication protocols) that can be used to communicate wirelessly with nearby devices. In some cases, the communications interfaces can include direct interfaces for particular sensors or general interfaces such as USB or firewire (e.g., as described above with respect to FIG. 7).

As used herein "storage media" do not consist of transitory, propagating waves. Instead, "storage media" refers to non-transitory media.

Prototype Example

A demonstration was performed using an excreta capture device connected to a commercial toilet such as illustrated in FIG. 1A, where the primary influent was in the form as illustrated in FIGS. 6A and 6B. Experiments were conducted with soybean paste surrogate of feces and human feces obtained from healthy volunteer under IRB protocol. Wet solid mass content was measured by drying according to a conventional total solid method. The dry solid was converted in wet solid using average moisture content of feces 75% and feces simulant of 50%. Following operations such as illustrated in FIGS. 4A-4D, the stools were immobilized in the primary influent and investigated by multi-modal sensor modalities. In tests for stool immobilization and removal, prototype designs provided an average of 92% immobilization efficiency in a rear exit toilet type over 90 tests and 90% immobilization efficiency in a bottom exit toilet type over 40 tests. A 90% removal efficiency was found over 39 tests. The presence of toilet paper was included in 8 tests, where 7 were successfully immobilized.

Tests were carried out to determine whether sufficient samples could be captured for use with various assays. Assays use a small amount of stool (~tenths of mg) and are typically tolerant of a range of value values. The Wet Solid Content (WSC) in mg solid/ml is a measure of the dilution of the solid amount in buffer.

For protein assays, to determine stool amount needed for a protein assay, a measurement was taken of the amount of solid collected by a commercial occult blood test, which was in the range of 12 to 124 mg (n=12) on different consistency samples; resulting in average solid content of WSC=10 or 25 mg/ml for the assay.

Microbiome molecular tests for the very abundant microbiome genome require a smaller sample amount. The study microbiome analysis was conducted with samples of estimated amount 1 mg of stool at a WSC=11 mg/ml solid content. In a pilot measurement on one stool, the liquefied specimen yield 64 ng/ul DNA, which is a quarter of the DNA (270 ng/ul) yielded by a scoop from the same stool.

For the DNA/RNA assay, molecular tests for detection of pathogens in stool recommend a mass of 50-200 mg and the protocol is for stool to be diluted 1:10 solutions and then clarified by centrifugation. The prototype system easily collected 15 ml, which at WSC=10 mg/ml results in 150 mg of mass for analysis.

The amount of solid to be extracted by the excreta capture device for each specimen can be tuned by water pressure in the stool erosion. For example, using a small pump connected to a precision flat fan nozzle, it was possible to tune the extracted specimen WSC between 10 to 50 mg/ml using different erosion pressure and time.

To demonstrate the feasibility of measuring of a GI disease biomarker from stool specimens extracted from the excreta capture device, occult (hidden) blood measurements using the Fecal Immunochemical Test (FIT) were conducted on liquified stool specimens.

The Second Generation FIT by Pinnacle Biolabs was used, with nominal cutoff at 50 ng/ml Hb in buffer (equivalent to 6 ug Hb/g feces, according to the manufacturer). Human hemoglobin spiked specimens were used in concentration of 3, 6, 10, 15 ug Hg/g feces. First, the nominal sensitivity of the kit was verified by obtaining a positive read-out of a 6 ug Hb/g spiked fecal specimen and negative read-out on unspiked control specimen. Then, results were plotted of positive, negative and "may be" read-out of the kit for a set of conditions varying the Hb concentration and the WSC in the specimen. Specimens spiked with 6 ug Hb/g and extracted in PBS results in positive assay, as expected, as long as WSC=>10 mg/ml. If WSC is high at 25 mg/ml, the kit is positive for lower hemoglobin concentration 3 ng/g. However, if both WSC and Hb are low, the test is negative. The test data demonstrate that for this FIT assay, stool specimen liquefied according with the proposed methods achieve the same analytical detection concentration as the conventionally prepared specimen. In addition, it is possible to automate the assay testing to avoid operating error and increase result consistency. The excreta capture device can automate the FIT test at the point of deposit by excluding sampling when visible blood is present and using machine vision to read the FIT cassette, avoiding operating error and increasing result consistency.

Detection of loose stools were also studied. Bowel movement that results in loose stools are defined by Bristol scale 6 (fluffy piece with ragged edges, mushy stool) and scale 7 (watery, no solid pieces). Bristol stool scale 7 bowel movement are hard to define by imaging alone in the immobilization area, because, in practical implementation, they will result in toilet paper with some brown material that may or may not be visible (but that will be extracted). Thus, an additional sensing modality was sought to detect loose stools to robustly identify this bowel movement. This is a particularly relevant functionality for health assessment, since the clinical definition of diarrhea is 3 loose stools within a period of 24 hours and diarrhea is a worrisome indicator.

Tests were conducted on established water quality indicators pH, electrical conductivity, ORP and turbidity for their suitability in differentiating stool from urine alone in a flush toilet. In a beaker water and human urine and feces were mixed in concentration emulating from one use in a flush toilet (0.03 g/ml feces, 0.08 ml/ml urine in water vol/vol). It was found that pH and ORP are not significantly different between urine and feces diluted in water, and electrically conductivity is dominated by the urine component, however EC is not helpful when loose stool and urination occur simultaneously. It was found that nephelometric turbidity, a light-scattering based measurement of the suspended particle in solution, is a sensitive measure of the presence of watery loose stool in a water solution. In particular, stools added to water that gets sampled after 1 minute result in turbidity values ranging from 10 to 120, significantly different from water (T=0.7 nephelometric turbidity unit NTU) and urine added to water (T=1.1±0.3 NTU, n=5 different specimens). Stool dissolved in water, that is a completely watery stool, results in saturation of the instrument >1000 NTU. It was found that it is possible to detect loose stools.

An analog turbidity probe with cables and board (SEN0189 by DF Robot) with nominal range 1200 NTUs, and its analog output connected to Arduino Uno board (DFRdruino UNO v3, DF Robot) was used for the prototype example. The Arduino was used to develop the sensors code and a laptop with the third-party software Teraterm to convert the data into a .CSV was used to log the turbidity sensor data. The SEN0189 signal was calibrated against the Hach 2100Q using solution obtained by dissolving a range of miso and it was found to be linear from T=0.7 NTU to T=905 NTU ($R^2$=0.9788). This is adequate since the sensor is used to provide a qualitative measure of the presence of stool.

Since human waste in toilet effluent often is mixed with toilet paper. The effect of toilet paper on the turbidity reading was evaluated and found to be negligible. For the tests, a proportion of toilet paper of 0.5 square per 100 ml of waste solution was used. This in equivalent to 30 toilet-paper-squares per use in a 6 L flush toilet. Static tests in a beaker with stool surrogates and toilet paper showed no effect of toilet paper on the measured values (two-tailed t-test P=0.54 with and with toilet paper, n=16 datapoints).

With the turbidity sensor installed, data was collected at 250 ms intervals of Bristol 7 stools (surrogate) and urine flushed by toilet. While the turbulence created by flush results in short noise spikes during urine flush, the passage of a turbid solution creates a signature of a multi-second dips in the turbidity sensor read-out that can be used to develop automatically calculated metric associated with loose stool.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. An excreta sample capture device comprising:
   a primary influent pipe that receives influent from one or more toilets;
   a first valve positioned at a downstream end of the primary influent pipe; and
   a second valve positioned underneath and between an upstream end of the primary influent pipe and the downstream end of the primary influent pipe;
   an optical imaging sensor or a camera;
   a sample extraction vessel located downstream of the second valve;
   a spray jet positioned above the second valve;
   a controller and one or more storage media having instructions stored thereon that when executed by the controller, direct the controller to at least:
   initiate closing of the first valve;
   capture, via the optical imaging sensor or the camera, an image of the influent;
   determine, from the captured image of the influent, a Bristol scale value of excreta within the influent;
   adjust, based on the determined Bristol scale value of the excreta within the influent, a pressure of a jet of liquid provided via the spray jet;
   provide, via the spray jet, the pressure adjusted jet of liquid across the excreta within the influent to cause liquification of at least some of that excreta; and
   collect, via the sample extraction vessel, a sample of the excreta that is liquified by the pressure adjusted jet of liquid.

2. The device of claim 1, wherein the instructions further direct the controller to
   initiate opening of the second valve prior to collecting the excreta that is liquified by the pressure adjusted jet of liquid.

3. The device of claim 2, further comprising:
   a sensor located upstream of the second valve; and
   instructions that direct the controller to receive, via the sensor, an indication that the influent containing the excreta is being received in the primary influent pipe.

4. The device of claim 3, wherein the sensor is a turbidity sensor.

5. The device of claim 3, further comprising instructions that direct the controller to determine, from the indication received via the sensor, a consistency of the excreta.

6. The device of claim 1, further comprising:
   a third valve positioned upstream of the first valve; and
   a secondary influent pipe positioned underneath the third valve that reconnects to piping downstream of the primary influent pipe.

7. The device of claim 6, wherein the third valve is radially adjacent to the second valve and the secondary influent pipe is sized to permit liquid, but not solids, to pass through.

8. The device of claim 1, further comprising at least one of an optical sensor, a gas sensor, an acoustic sensor, or a thermal sensor.

9. A method of using an excreta sample capture device, comprising:
   receiving influent in a primary influent pipe;
   initiating a closing of a first valve positioned at a downstream end of the primary influent pipe;
   capturing, via an optical imaging sensor or camera, an image of the influent;
   determining, from the captured image of the influent, a Bristol scale value of excreta within the influent;
   adjusting, based on the determined Bristol scale value of the excreta within the influent, a pressure of a jet of liquid provided via a spray jet positioned above a second valve;
   providing, via the spray jet, the pressure adjusted jet of liquid across the excreta within the influent to cause liquification of at least some of that excreta;
   opening the second valve positioned underneath and between an upstream end of the primary influent pipe and the downstream end of the primary influent pipe; and collecting, via a sample extraction vessel positioned downstream of the second valve, a sample of the excreta that is liquified by the pressure adjusted jet of liquid.

10. The method of claim 9, further comprising:
opening a third valve positioned upstream of the first valve until liquid from the influent has been drained from the primary influent pipe;
closing the third valve.

11. The method of claim 10, wherein the third valve is radially adjacent to the second valve.

12. The method of claim 9, further comprising:
closing the second valve;
opening the first valve; and
providing a sufficient amount of water to flush any remaining excreta downstream of the first valve.

13. One or more storage media having instructions stored thereon that when executed by a controller, direct the controller to at least:
in response to receiving influent in a primary influent pipe, close a first valve positioned at a downstream end of the primary influent pipe;
capture, via an optical imaging sensor or a camera, an image of the influent;
determine, from the captured image of the influent, a Bristol scale value of excreta within the influent;
adjust, based on the determined Bristol scale value of the excreta within the influent, a pressure of a jet of liquid provided via a spray jet positioned above a second valve;
open the second valve positioned underneath and between an upstream end of the primary influent pipe and the downstream end of the primary influent pipe;
provide, via the spray jet positioned above the second valve, the pressure adjusted jet of liquid across the excreta within the influent to cause liquification of at least some of that excreta; and
collect, via a sample extraction vessel located downstream from the second valve, a sample of the excreta that is liquified by the pressure adjusted jet of liquid.

* * * * *